(12) United States Patent
Varghese et al.

(10) Patent No.: US 10,850,274 B2
(45) Date of Patent: Dec. 1, 2020

(54) MICROFLUIDIC ASSISTED PERFUSION DEVICES

(71) Applicant: The Regents of the University of California, Oakland, CA (US)

(72) Inventors: Shyni Varghese, La Jolla, CA (US); Aereas Aung, San Diego, CA (US); Han Liang Lim, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 81 days.

(21) Appl. No.: 15/564,617

(22) PCT Filed: Apr. 9, 2016

(86) PCT No.: PCT/US2016/026840
§ 371 (c)(1),
(2) Date: Oct. 5, 2017

(87) PCT Pub. No.: WO2016/164861
PCT Pub. Date: Oct. 13, 2016

(65) Prior Publication Data
US 2018/0085750 A1    Mar. 29, 2018

Related U.S. Application Data

(60) Provisional application No. 62/145,900, filed on Apr. 10, 2015.

(51) Int. Cl.
*C12M 3/06* (2006.01)
*C12N 5/00* (2006.01)
*B01L 3/00* (2006.01)

(52) U.S. Cl.
CPC ....... *B01L 3/502707* (2013.01); *C12M 23/16* (2013.01); *C12N 5/0012* (2013.01); *B01L 2300/123* (2013.01); *C12N 5/0062* (2013.01); *C12N 2533/30* (2013.01); *C12N 2533/40* (2013.01); *C12N 2533/54* (2013.01)

(58) Field of Classification Search
CPC .............. B01L 3/502707; C12M 23/16; C12N 5/0062; C12N 2533/54; C12N 2533/40
See application file for complete search history.

(56) References Cited

U.S. PATENT DOCUMENTS

| | | | |
|---|---|---|---|
| 8,241,656 B2 * | 8/2012 | Chudzik | A61K 9/0024 424/426 |
| 2013/0137155 A1 | 5/2013 | Morgan et al. | |
| 2014/0212910 A1 | 7/2014 | Bhatia et al. | |

OTHER PUBLICATIONS

Khetan and Burdick, Soft Matter, 2011, vol. 7, p. 830-838.*
Nichol et al., Biomaterials, 2010, vol. 31, p. 5536-5544.*
Du et al., PNAS, 2008, vol. 15, No. 28, p. 9522-9527.*
Chueh et al., Biomed. Microdevices, 2010, vol. 12, p. 145-151.*
Young, Lee W., International Search Report & Written Opinion, PCT/US2016/026840, United States Patent & Trademark Office, dated Jul. 26, 2016.

* cited by examiner

*Primary Examiner* — Kade Ariani
(74) *Attorney, Agent, or Firm* — Gavrilovich, Dodd & Lindsey LLP

(57) ABSTRACT

The disclosure provides for microfluidic devices comprising patterned hydrogels with embedded cells or microtissues.

24 Claims, 18 Drawing Sheets

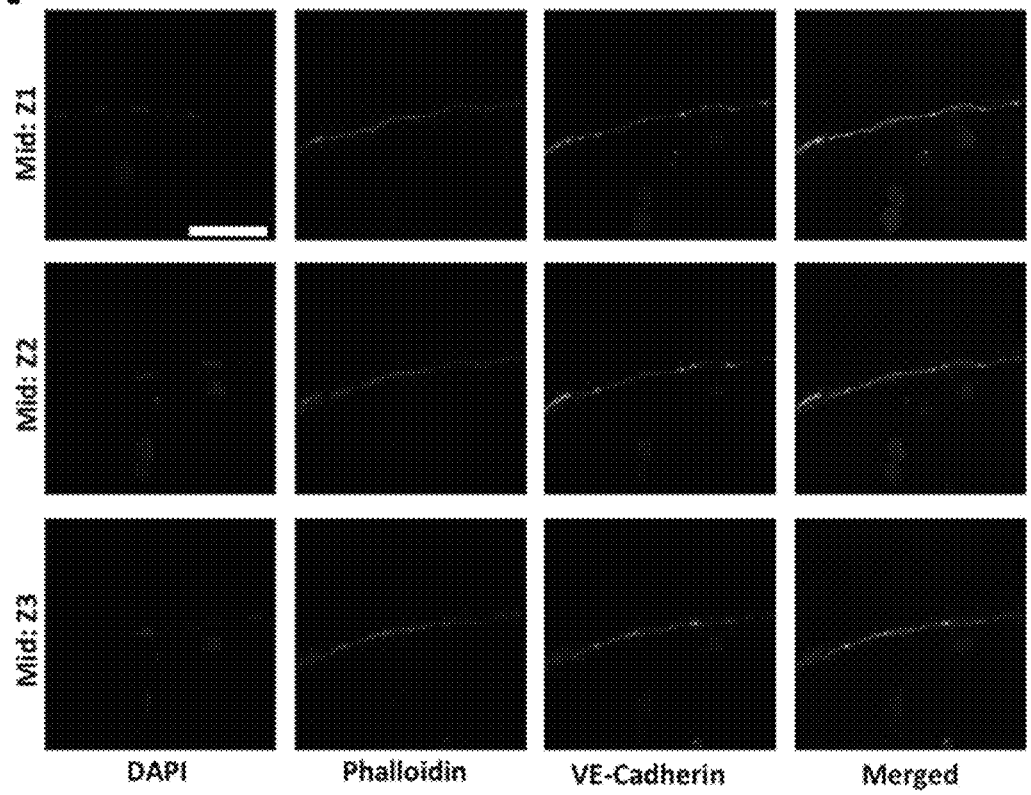
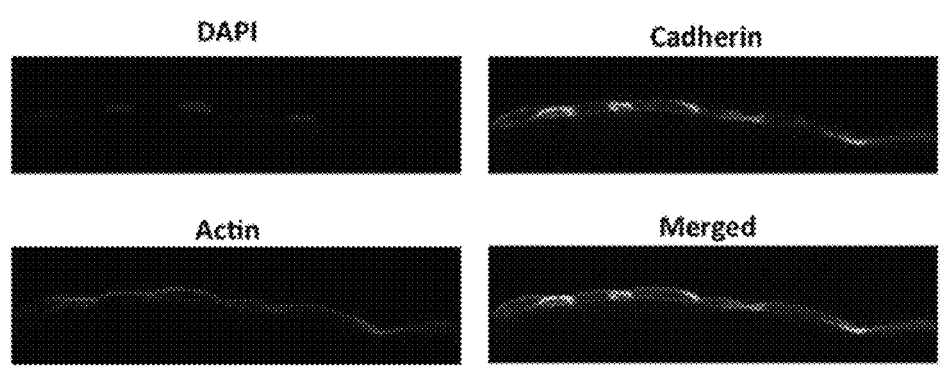
FIG. 17A-B

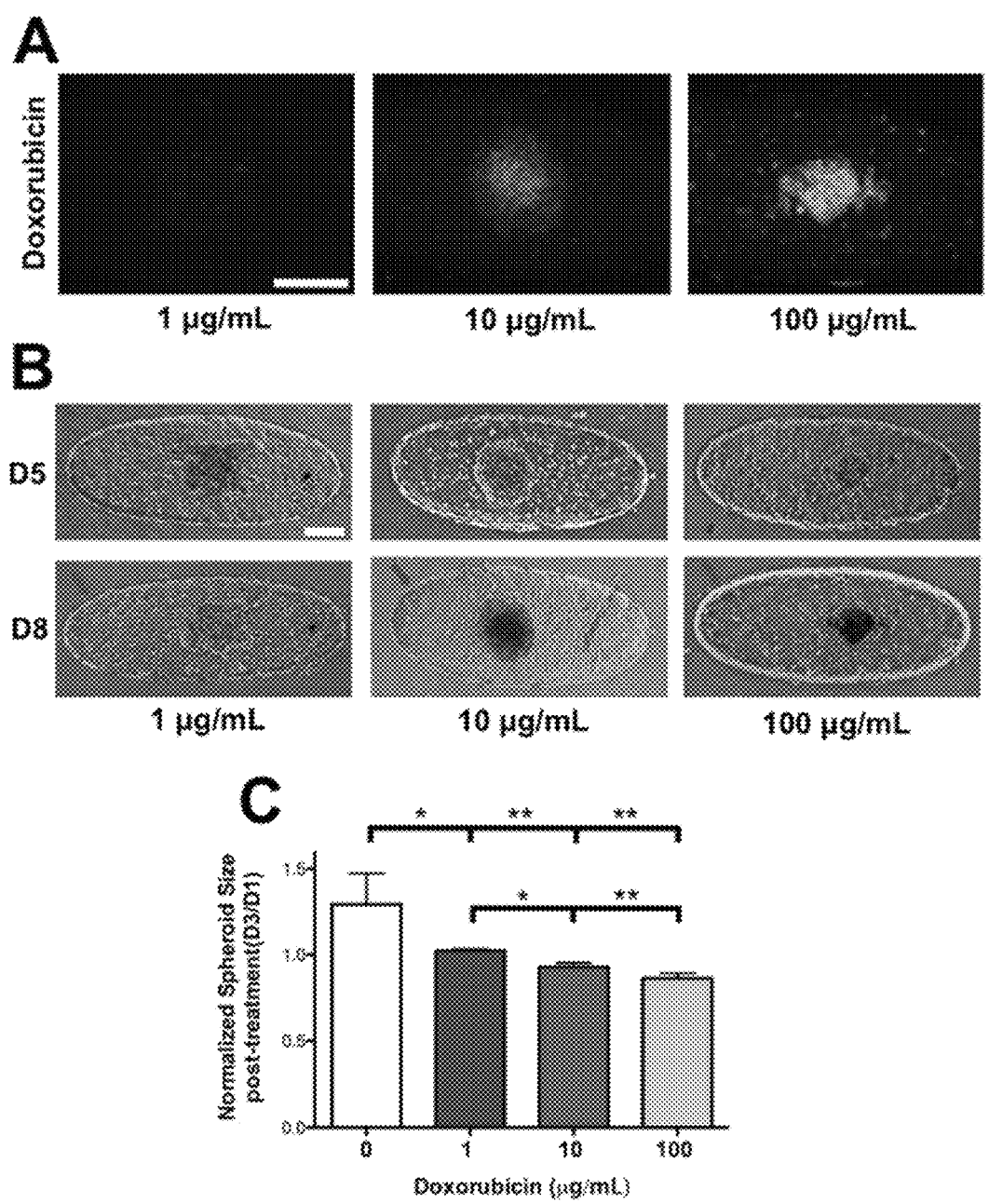
FIG. 18A-C

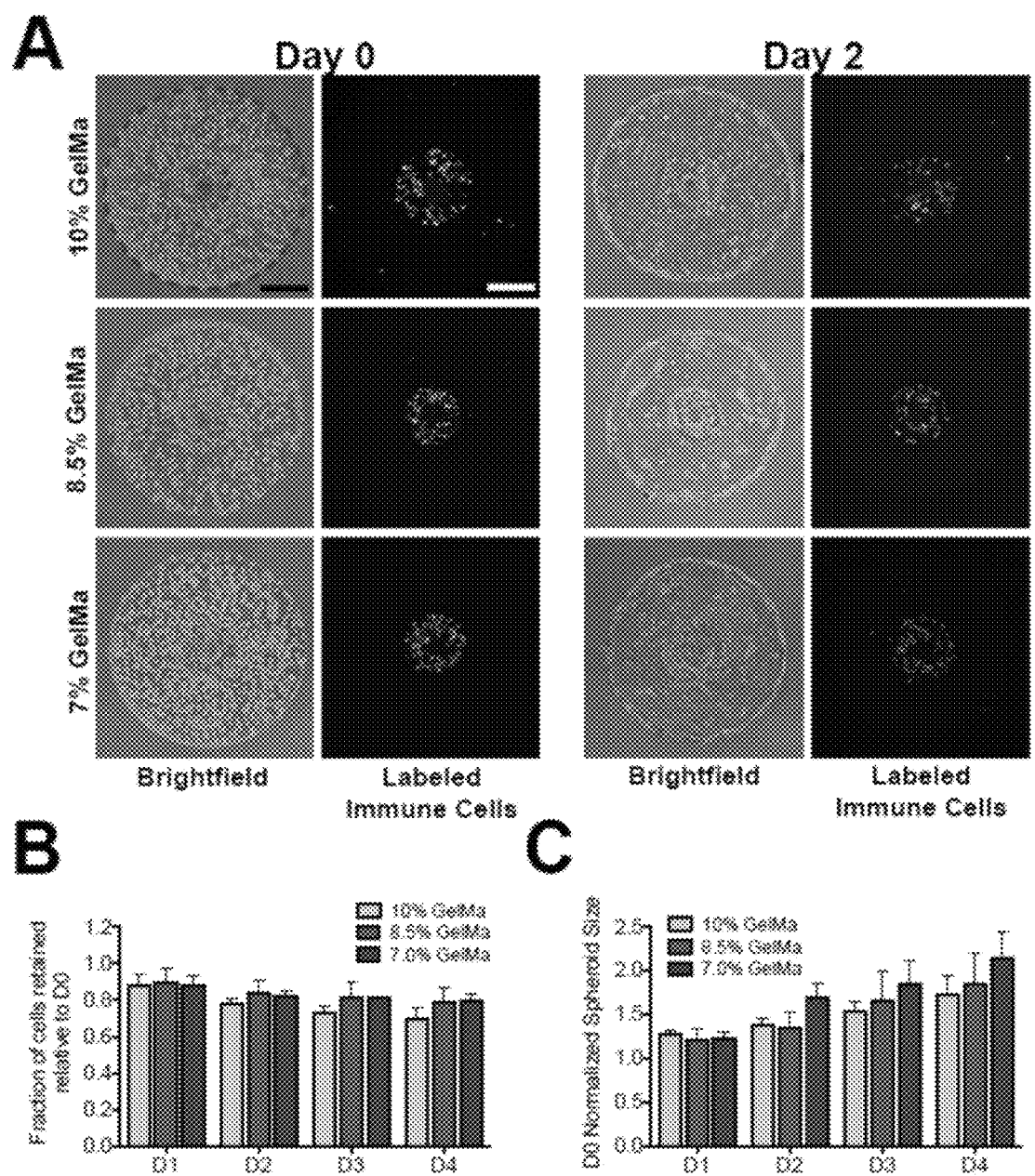
FIG. 20A-C

MICROFLUIDIC ASSISTED PERFUSION DEVICES

CROSS REFERENCE TO RELATED APPLICATIONS

This application is a U.S. National Stage Application filed under 35 U.S.C. § 371 and claims priority to International Application No. PCT/US2016/026840, filed Apr. 9, 2016, which application claims priority under 35 U.S.C. § 119 from Provisional Application Ser. No. 62/145,900, filed Apr. 10, 2015, the disclosures of which are incorporated herein by reference.

STATEMENT REGARDING FEDERALLY SPONSORED RESEARCH

This invention was made with Government support under Grant No. AR063184, awarded by the National Institutes of Health. The Government has certain rights in the invention.

TECHNICAL FIELD

The disclosure provides for microfluidic devices comprising patterned hydrogels with embedded cells or microtissues.

BACKGROUND

Current drug development protocols rely on testing in 2D monolayer cultures and animal models during the preclinical stage to assess for drug efficacy and cellular toxicity. It has been shown however, that monolayer cultures may be inadequate for drug testing purposes since in vivo cells are often embedded within extracellular matrices and display cell surface receptor characteristics that are not recapitulated in monolayer cultures.

According to the American Cancer Society, cancer is the second leading cause of death in the United States where one in four deaths in 2015 were cancer-related. Despite such grim outlooks, survival rate amongst cancer patients has steadily increased from 49% to 68% over the past decade due to the increase in our fundamental understanding of this disease and technological advances.

SUMMARY

The disclosure provides a method for in vitro cell culture and screening comprising (a) providing a cellular composition comprising cells in a polymerizable media; (b) providing a microfluidic device, comprising: (i) an inlet channel; (ii) an outlet channel; (iii) a cell culture chamber fluidly connected between the inlet and outlet, wherein the chamber comprises a biocompatible layer for cell binding; (c) identifying cellular islands; and (d) polymerizing the islands with UV light. In one embodiment, the cellular composition comprises stromal cells. In another or further embodiment, the cellular composition comprises parenchymal cells. In still a further embodiment, the stromal cells are fibroblasts. In yet another embodiment, the parenchymal cells are cancer cells. In another embodiment of any of the foregoing embodiments, the cellular composition comprises a polymerizable media of gelatin methacrylate with an ascorbic acid and a photoinitiator. In another embodiment, the cell culture chamber comprises opposing surfaces coated with polyacrylamide and methacrylate. In yet another embodiment, the cell culture chamber is optically translucent or transparent. In another embodiment, the method further comprises contacting the cellular islands with a test agent. In a further embodiment, the cellular composition comprises cancer cells and the test agent is an anticancer agent. In yet another embodiment, the cell culture chamber comprises patterned hydrogels of natural polymers which comprise photoreactive side groups. In yet another embodiment, the cell culture composition comprises natural polymers with photoreactive side groups. In a further or alternative embodiment, the natural polymers are selected from hyaluronic acid, gelatin, chitosan, and cellulose. In yet another alternate embodiment, the photoreactive side groups are cinnamate groups, acrylate-based groups, or combination thereof. In another embodiment of any of the foregoing, the cellular islands comprise gelatin methacrylate. In another embodiment, the polymerized islands comprise cells or microtissues embedded within the polymerized island. In a further embodiment, the cells are cancerous cells. In another embodiment, the cells or microtissues are from the digestive system, musculoskeletal system, respiratory system, urinary system, reproductive system, endocrine system, cardiovascular system, lymphatic system, nervous system, or integumentary system. In yet another embodiment, the cells or microtissues are from the liver, heart, or skeletal muscle. In still another embodiment, the cells are stem or progenitor cells. In another embodiment of any of the foregoing embodiments, the cells are genetically engineered. In another embodiment of any of the foregoing embodiments, the islands are polymerized by a photomask-based stereolithography approach coupled with the photogelation of polymers. In another embodiment, the cell culture chamber further comprises a top hydrogel attached or tethered to the top of the chamber. In yet another embodiment, the cell culture chamber comprises a bottom hydrogel attached or tethered to the bottom of the chamber. In another embodiment of any of the foregoing embodiments, the cell culture chamber comprises a polymer that is inert and resists re-molding by cells. In a further embodiment, the polymer is polyacrylamide. In another embodiment, the cellular compositions comprises endothelial cells and wherein the polymerized islands are contacted with flowing media, whereby the endothelials cells migrate to the periphery of the cellular island forming an endothelial barrier around the island. In other embodiment, the cell composition comprises a hydrogel precursor solution containing a photoinitiator and suspended cells. In still a further embodiment, the cell composition is introduced into the cell culture chamber. In a further embodiment, part (c) and (d) comprise identifying cellular islands; forming a patterned hydrogel comprising the cellular islands by using a photomask which is placed under the fluidics chamber of the device, and a UV light of a wavelength of about 365±40 nm is shone onto the cellular island; and removing excess unreacted hydrogel precursor solution from the fluidics chamber by washing with a buffered solution.

The disclosure also provides a method of for fabricating the microfluidic device of the disclosure, comprising polymerizing a first hydrogel precursor solution containing a chemical initiator and optionally fluorescent particles onto surface of a first substrate and second substrate that have been chemically activated with glutaraldehyde or methacrylate in order to form a first hydrogel on the first substrate and second hydrogel on the second substrate; forming a polydimethylsiloxane (PDMS) mold comprising the hydrogel of the first substrate; puncturing the PDMS mold to provide inlet and outlet flow paths; treating the second substrate comprising the second hydrogel and the PDMS mold comprising the first hydrogel with UV-Ozone; bonding the PDMS mold to the second substrate at an elevated temperature to form a fluidics chamber, wherein the bond is chemically and irreversibly formed. The method further comprises equilibrating the first and second hydrogel to physiological pH and osmolarity by using a buffered solution.

The disclosure also provides a method for determining the effects of a pharmaceutically active agent on cells or microtissues comprising introducing the pharmaceutically active agent in a carrier into the microfluidics device of claim 1, and comparing the effects of the agent on the cells or microtissues in comparison to the carrier alone.

The disclosure also provides a device comprising cell containing polymerized hydrogel islands in microfluidic system, wherein the islands are selectively patterned. In one embodiment, the selectively patterned islands provide a microtissue comprising cellular islands of different cell types.

The disclosure provides for a microfluidic device comprising a chamber comprising one or more patterned hydrogels, and an inlet and an outlet channel, which then branches off into multiple channels to perfuse the entire chamber. Various geometrical features can be achieved by using a photomask to limit the spatial distribution of UV light, which results in the polymerization of the hydrogel solution only in the exposed regions. In particular embodiments, the microfluidic device further comprises a ceiling hydrogel and a floor hydrogel. In further embodiments, the patterned hydrogel is in contact with the ceiling hydrogel and/or the floor hydrogel to form a "gel-on-gel" sandwich. In additional embodiments, the microfluidic device may further comprise cells or microtissues embedded in the one or more patterned hydrogels. Complexities in the microtissues can be achieved by using various hydrogel precursor solutions containing different polymers or different cells, and then exposing them in sequence.

The disclosure further provides that the microfluidic device disclosed herein may be used in a variety of applications, including drug testing and small molecule screening. For example, drugs or small molecules can be solubilized in media and infused into a chamber comprising cells or microtissues embedded in patterned hydrogel(s). The effects of the drug or small molecule on the cells or microtissues can then be assayed. The assays can be performed in real-time without perturbing the microfluidic system. Additionally, the mechanical behavior of the microtissues can be studied. For example, the mechanical behavior of microtissues can be tracked by the real-time displacements of the fluorescent particles embedded within the ceiling and floor hydrogels and measuring the forces generated by the contractile tissues. Additionally, by collecting media that elutes from the outlet port, one can test for: (1) changes in the metabolism by measuring the differences in metabolites between the inlet and outlet ports, and (2) chemical or biochemical signaling molecules that are being secreted by the cells or microtissues.

The disclosure also provides methods to fabricate patterned hydrogels, which are micron-sized constructs of natural or artificial biocompatible polymers which can support cells growing within or around it. In a further embodiment, the disclosure provides methods of incorporating the patterned hydrogels into a microfluidic device. In certain embodiments, the fabrication method comprises a patterning step using a photolithographic method to control the spatial distribution of both the hydrogel and cells, allowing for varying geometries. A microfluidic system comprising the microfluidic device can be utilized to perfuse any characteristic fluid through the device, allowing for interactions between fluid constituents and microtissues, which can be further analyzed. The methods disclosed herein allow for the inclusion of multiple cell types within chamber(s) of the microfluidic device.

In a particular embodiment, the disclosure provides for a microfluidic device comprising: a chamber which comprises one or more patterned hydrogels, wherein the patterned hydrogel(s) are biocompatible with cells; an inlet channel; an outlet channel; and multiple channels that can perfuse the chamber, wherein the multiple channels, inlet channel and outlet channel are in fluid contact. In a further embodiment, the one or more patterned hydrogels are comprised from natural polymers which comprise photoreactive side groups. Examples of natural polymers include, but are not limited to, hyaluronic acid, gelatin, chitosan, and cellulose. Examples of photoreactive side groups include, but are not limited to, cinnamate groups, acrylate-based groups, or combination thereof. In a certain embodiment, the patterned hydrogel(s) are comprised of gelatin methacrylate.

In a particular embodiment, the patterned hydrogel of a microfluidic device disclosed herein comprises cells or microtissues embedded within the patterned hydrogel. In another embodiment, the cells are cancerous cells. In yet another embodiment, the cells or microtissues are from the digestive system, musculoskeletal system, respiratory system, urinary system, reproductive system, endocrine system, cardiovascular system, lymphatic system, nervous system, or integumentary system. In a further embodiment, the cells or microtissues are from the liver, heart, or skeletal muscle. In yet a further embodiment, the cells are stem or progenitor cells.

In a certain embodiment, the disclosure provides that the patterned hydrogels of a microfluidic device of the disclosure are by using by a photomask-based stereolithography approach coupled with the photogelation of polymers.

In a particular embodiment, the disclosure also provides for a microfluidic device which comprises a top hydrogel attached or tethered to the top of the fluidics chamber, and/or a bottom hydrogel attached or tethered to the top of the fluidics chamber. In a further embodiment, the patterned hydrogel is in contact with the top hydrogel, the bottom hydrogel, or both the top and bottom hydrogels. In another embodiment, the top hydrogel and/or bottom hydrogel are made of polymer that is inert and resists re-molding by cells, such as polyacrylamide.

In a certain embodiment, the disclosure further provides a method for fabricating a microfluidic device of the disclosure, comprising: polymerizing a first hydrogel precursor solution containing a chemical initiator and optionally fluorescent particles onto surface of a first substrate and second substrate that have been chemically activated with glutaraldehyde or methacrylate in order to form a first hydrogel on the first substrate and second hydrogel on the second substrate; forming a polydimethylsiloxane (PDMS) mold comprising the hydrogel of the first substrate; puncturing the PDMS mold to provide inlet and outlet flow paths; treating the second substrate comprising the second hydrogel and the PDMS mold comprising the first hydrogel with UV-Ozone; bonding the PDMS mold to the second substrate at an elevated temperature to form a fluidics chamber, wherein the bond is chemically and irreversibly formed; equilibrating the first and second hydrogel to physiological pH and osmolarity by using a buffered solution; introducing a second hydrogel precursor solution containing a photoinitiator and suspended cells into the fluidics chamber; forming a patterned hydrogel comprising cells by using a photomask which is placed under the fluidics chamber of the device, and a UV light of wavelength 365±40 nm is shone from underneath; and removing excess unreacted hydrogel precursor solution from the fluidics chamber by washing with a buffered solution.

In a particular embodiment, the disclosure provides a method for determining the effects of a pharmaceutically active agent on cells or microtissues comprising: introducing the pharmaceutically active agent in a carrier into a microfluidics device disclosed herein, and comparing the effects of the agent on the cells or microtissues in comparison to introducing the carrier alone.

DESCRIPTION OF DRAWINGS

FIG. 17A-B shows immunostaining of HUVECs cells migrated to the periphery of the GelMA structure. (A) X-Y confocal sections of HUVECs cells stained for F-Actin and nuclei at different Z positions: GelMA-PAm interface (labeled as Top and Bottom) and middle of the GelMA hydrogel (labeled as Mid). Green fluorescent beads were embedded within the PAm hydrogels to visualize the presence of the hydrogels. The rows indicate the specified Z positions. The columns 1-3 indicate the specific color channel while column 4 displays the merged image from other channels. Scale bar: 100 μm. (B) High magnification X-Y sections of HUVECs stained for VE-Cadherin, F-Actin, and nuclei at the midsection of the GelMA hydrogel. Scale bar: 10 μm. The HUVECs in both images were cultured with MCF7 spheroids for 5 days within the fluidics device prior to staining.

FIG. 18A-C shows dose-dependent response of encapsulated tumor spheroids to Doxorubicin. (A) Fluorescent images to identify Doxorubicin penetration into the cancer spheroids at D8. Increased penetration of Doxorubicin into the MCF7 spheroid is observed at higher dosages. Scale bar: 200 μm. (B) Bright field images of HUVECs and MCF7 spheroids prior to (D5) and 3 days after Doxorubicin treatment (D8). Red arrow points towards the presence of endothelial barrier and the lack thereof at and above 10 μg/mL of Doxorubicin, respectively. Scale Bar: 200 μm. (C) Change in spheroid size of MCF7 after Doxorubicin treatment for different dosages of Doxorubicin. The spheroid area, obtained from 2-D bright field images, at D8 is normalized to the area at D5. * and ** indicate statistically significant differences of p<0.05 and 0.01, respectively, as obtained from pair wise t-test.

FIG. 20A-C shows formation and effect of structures with spatially mechanical properties on encapsulated cells. (A) The inner cylindrical hydrogel (red dashed line), containing cancer spheroids and immune cells, was created using 7.0% GelMa precursor solution. Since the additive approach allows for a different precursor solution along with different cells to be introduced into the device, the larger cylindrical hydrogel (blue dashed line) was created from 7, 8.5, or 10% GelMa precursor solution to achieve a composite structure with controlled mechanical properties. The bright field and labeled immune cells within the hydrogel structures are shown at Day 0 and Day 2. The effect of exterior GelMa concentration in the exterior hydrogel on immune cell retention and cancer spheroid growth is shown in (B) and (C). (B) Although minor, decreasing GelMa concentration in the exterior hydrogel retains a higher fraction of immune cells. (C) On the other hand, a significant increase in cancer spheroid growth can be observed with decreasing GelMa concentration when comparing 7.0% to 10%.

DETAILED DESCRIPTION

Figure 1:
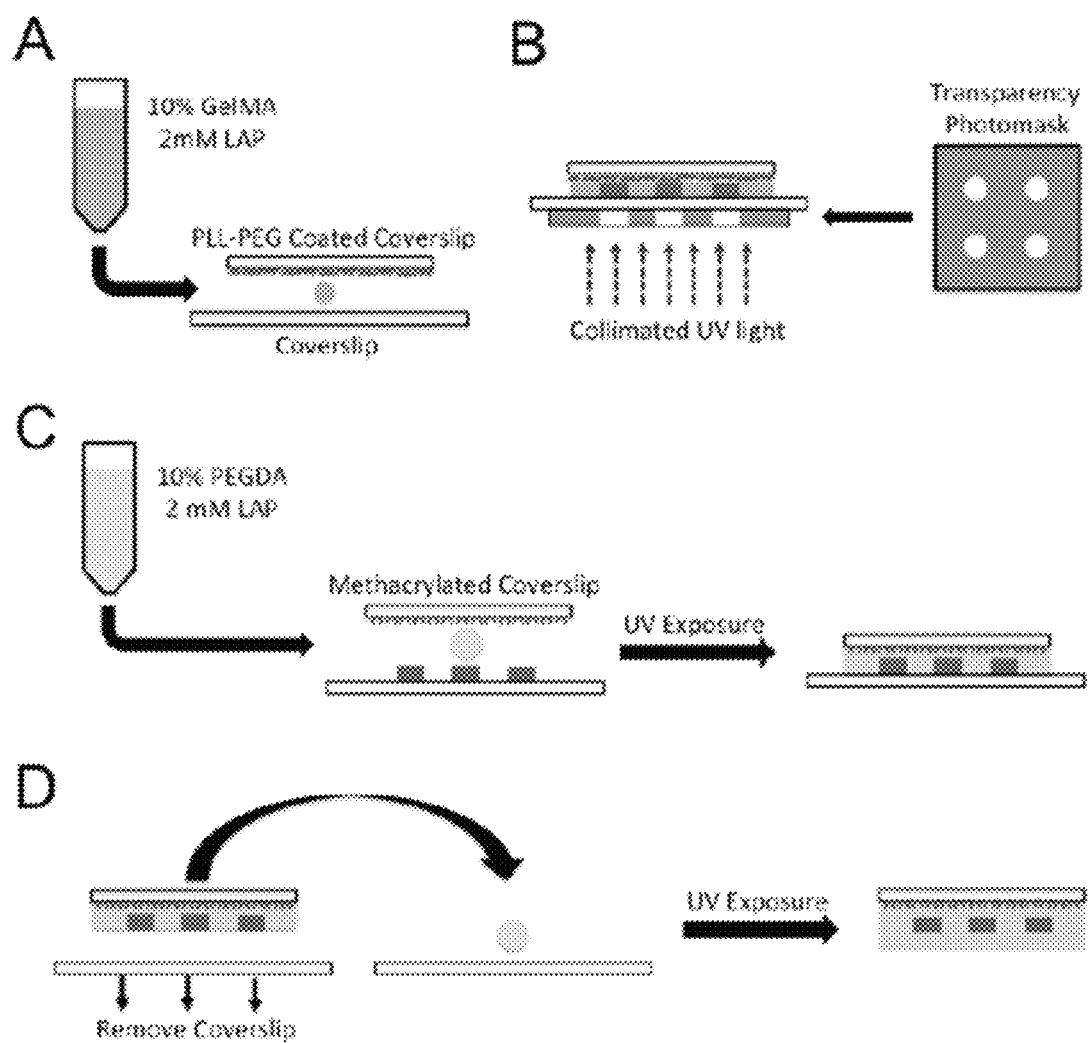
FIG. 1A-D demonstrates an embodiment of patterning a hydrogel. (A) The gelatin methacrylate (GelMa) solutions supplemented with lithium phenyl-2,4,6-trimethylbenoyl-phosphinate (LAP) and fluorescent particles were sandwiched between polylysine grafted polyethylene glycol (PLL-PEG) treated and regular coverslips, which is exposed to a collimated UV light through a photomask printed with the desired patterns. The PLL-PEG treatment is used to promote adhesion of the hydrogel onto the regular coverslip. (B) The non-irradiated regions are then washed off to leave behind the 3D patterned GelMA structures. (C) To embed the 3D patterned structures within another hydrogel, the GelMA structures formed on the glass coverslip is immersed within PEGDA solution containing LAP. The PEGDA solution is then photopolymerized, whereby the PEGDA solution is sandwiched between the GelMA layer and a methacrylated glass coverslip prior to gelation. The use of methacrylated coverslip ensures the detachment of the GelMA structures after they are embedded within the PEGDA hydrogels. (D) To achieve the complete embedment of the GelMA structures, the above-mentioned procedure was repeated using a glass coverslip that was not methacrylated.

As used herein and in the appended claims, the singular forms "a," "and," and "the" include plural referents unless the context clearly dictates otherwise. Thus, for example, reference to "a hydrogel" includes a plurality of such hydrogels and reference to "the microtissues" includes reference to one or more microtissues and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although many methods and reagents similar or equivalent to those described herein can be used in the practice of the disclosed methods and compositions, the exemplary methods and materials are now described.

All publications mentioned herein are incorporated herein by reference in their entirety for the purposes of describing and disclosing methodologies that might be used in connection with the description herein. Moreover, with respect to any term that is presented in one or more publications that is similar to, or identical with, a term that has been expressly defined in this disclosure, the definition of the term as expressly provided in this disclosure will control in all respects.

Over the past decade, many in vitro models for drug screening have been developed. These models, however, either lack physiologically relevant complexity or are limited in their throughput. More recently, microfluidic organ-on-chip devices have emerged as one of the methods to achieve high throughput capabilities that also allow for the monitoring of drug activity in real time. However, existing systems do not allow for the precise spatial control of cells. Further, the devices do not allow for the measurement of contractile forces in real time, an integral indicator of healthy cells (e.g., cardiac function and drug responsiveness). Controlling cell seeding in 3D tissue constructs within a perfusion-based device allows for real-time readouts of data. Real-time contractile force monitoring, for example, is currently not available by using microfluidic or other devices taught in the art. The microfluidic device of the disclosure, however, provides for real-time monitoring of biological and physiological responses and behaviors of cells.

The integration of 3D cell cultures with microfluidics technology can be used to create tumor models with perfusion to facilitate mass transport. Such microfluidic devices can be used to study various aspects of cancer progression such as tumor growth, presence of high interstitial fluid pressure, and cancer cell extravasation. Such technological platforms can also be used to understand drug-tumor interactions such as drug specificity, penetration into cancer spheroids, and efficacy towards repressing cancer growth. Existing platforms employ multi-layered or multi-channel devices to create a perfused tumor-a-on-chip system. Generation of such integrative fluidic system often requires multiple steps and complex fabrication processes.

The ability to seed or encapsulate cells within biomaterials like hydrogels has been widely used to achieve three-dimensional (3D) culture of cells. Significant progress has been made over the years to engineer hydrogel matrices with tissue-specific mechanical and biochemical properties. Recapitulating the heterogeneity and architectural complexity of native tissues in hydrogel scaffolds is of particular interest. To this end, a number of patterning and printing techniques have been developed. Some of these include nozzle-based printing, DMD projection patterning, and laser-based stereolithography to create 3D structures and methods to introduce required features into preexisting 3D structures.

The disclosure provides a photomask-based stereolithography approach coupled with the photogelation of polymers to create patterned 3D structures, which can be reinforced with one or more surrounding hydrogel layers. The disclosure provides a simple approach to create a culture on chip device, e.g., tumor-on-a-chip (TOC) device. For example, the TOC device can contain tumor spheroids within an artificial extracellular matrix surrounded by a single-celled endothelial barrier that is assembled through vascular endothelial (VE)-cadherin junctions. Specifically, cancer spheroids along with human umbilical vein endothelial cells (HUVECs) were confined within gelatin methacrylate (GelMA) hydrogel structures through 3D photopatterning and integrated into a microfluidic device. The differential motility of cancer spheroids and endothelial cells in response to chemotactic gradients generated within the 3D environment was harnessed to drive the migration of endothelial cells to the periphery to form a barrier surrounding the cell-laden GelMA structures. The disclosure further demonstrates the validation of this tumor-on-a-chip device as a drug-screening platform by using Doxorubicin, a commonly used anti-cancer drug, as a model compound.

The disclosure provides for an innovative microfluidic device comprising a microfluidic chamber comprising a patterned hydrogel (e.g., gelatin methacrylate (GelMA)) containing three dimensional and functional microtissues and/or cells, and an inlet and an outlet channel. The channels can branch off into multiple channels to perfuse the entire chamber. The hydrogels can be patterned by using a photolithography method that can control the geometries and dimensions of the resulting hydrogels (e.g., polymerized hydrogel cell islands). Moreover, the photopolymerization of the hydrogel allows for the encapsulation of cells within the hydrogel. The patterned hydrogel facilitates cell adherence, migration, proliferation and organization of the encapsulated cells. The patterned hydrogel can be any photopolymerizable biomaterial, including synthetic polymers, such as poly(ethylene glycol) (PEG) diacrylate, (PEG) dimethyacrylate, poly(propylene fumarate-co-ethylene glycol), acrylic modified PVA; and natural polymers, such as hyaluronic acid, gelatin, chitosan, and cellulose, which have been modified to provide photoreactive groups (e.g., cinnamate groups, methacrylate groups, etc.). Typically and preferably the hydrogels are biocompatible. The microfluidic devices of the disclosure can therefore spatially confine microtissues having specific geometries and cell types in order to replicate in vivo organ systems. Further, unlike the 3D printed constructs typically used in static culture systems, the patterned hydrogels of the disclosure have been incorporated into a dynamic flow process within a microfluidic device. The dynamic flow can then be used to replicate important physiological conditions, such as shear stress and pulsatile flow, and can further serve as a delivery system for natural or synthetic molecules by mimicking the circulatory system of the human body. Additionally, in contrast to organ-on-chips devices that use 2D tissue monolayers, the patterned hydrogels of the disclosure provide a scaffold for 3D functional microtissues.

In further embodiments, the disclosure provides that the microfluidic device comprises hydrogels that have been integrated into the cell culture chamber to form, coat, or project from the ceiling, floor and one or more sides of the chamber. These hydrogels can be made of the same material as the patterned hydrogel, or alternatively be made of a different material. In a particular embodiment, the hydrogels are bio-inert and resist remolding by cells. A photolithography method can be used to photopolymerize and encapsulate cells in the patterned hydrogels located between ceiling and floor hydrogels to create a "gel-on-gel sandwich". The "gel-on-gel sandwich" provides certain benefits including: the tuning of the chemical compositions and physical properties of the floor and ceiling hydrogels allows for real-time on-chip sensors responsive to changes in temperature, pH, electric field, and cell generated forces within the device; and (2) the structural integrity of the 3D microtissues embedded in a biodegradable polymer can be maintained by incorporating anti-fouling monomers into the ceiling and floor hydrogels, thereby preventing the binding of proteins to the chamber surfaces and preventing the migration of cells out of the patterned hydrogel.

In a particular embodiment, the microfluidic device is a cardiac-based microfluidic device that is capable of quantifying contractile forces in situ of cardiac cells. For these cardiac-based microfluidic devices, primary cardiomyocytes are encapsulated within a pattered hydrogel. The cardiomyocytes undergo many phases of remodeling in which both the cells and gel are remodeled, including actin filament recovery and filopodia extension, cell-adhesion molecular assembly, increased gap junctional protein expression, and finally contractile coupling to facilitate contractions. In certain embodiments, by sandwiching a patterned hydrogel comprising cardiac-microtissues between the ceiling and floor hydrogels, it is possible to calculate the magnitude of contractile forces using confocal microscopy and finite element analysis from the microtissues within the device. In a particular embodiment, the patterned hydrogel comprises cardiomyocytes embedded in a patterned gelatin methacrylate (GelMa) hydrogel. In a further embodiment, the ceiling and floor hydrogels of the cardiac-based microfluidic device are polyacrylamide (Pam) hydrogels.

The disclosure further provides that the cardiac-based microfluidic device comprises arrays of viable cardiac microtissues which display characteristics of cardiac function, including positive immunofluorescent staining and measurable contractile forces. In a set of assays presented herein, the microfluidic device promoted healthy cardiac microtissues formation allowing for the study of cardiac-specific tissue-environment interactions. By staining for connexin-43 it was found that the cardiac cells form gap junctions in the microfluidic system disclosed herein, allowing for the coordinated contraction within each construct. Connexin-43, found abundantly in cardiac tissue, is a member of a family of proteins that assembles to form gap junctions across the plasma membrane of cells, allowing for the exchange of small molecules, ions and second messengers. Thus, cell-cell communication facilitated by gap junctions is important in allowing for the synchronization of cardiac contractions. However, during the primary cell isolation process, it is difficult to isolate pure cardiomyocytes, leading to a heterogeneous cell mixture that includes primary fibroblasts in addition to cardiomyocytes. It has been shown that gap junctions formed by connexin-43 allow for the coupling of fibroblasts and cardiomyocytes. This allows for the propagation of electrical signals through the fibroblasts, leading to coordinated contraction of cardiomyocytes despite the fibroblasts not being capable of generating cardiac action potentials. Recently it has also been shown that fibroblasts may have important cardiac electrophysiological functions beyond acting as passive barriers that allow for normal electrical signal propagation. Thus, these staining images for connexin-43 as well as visual coordinated contractions indicate healthy cardiac microtissues.

Figure 5:
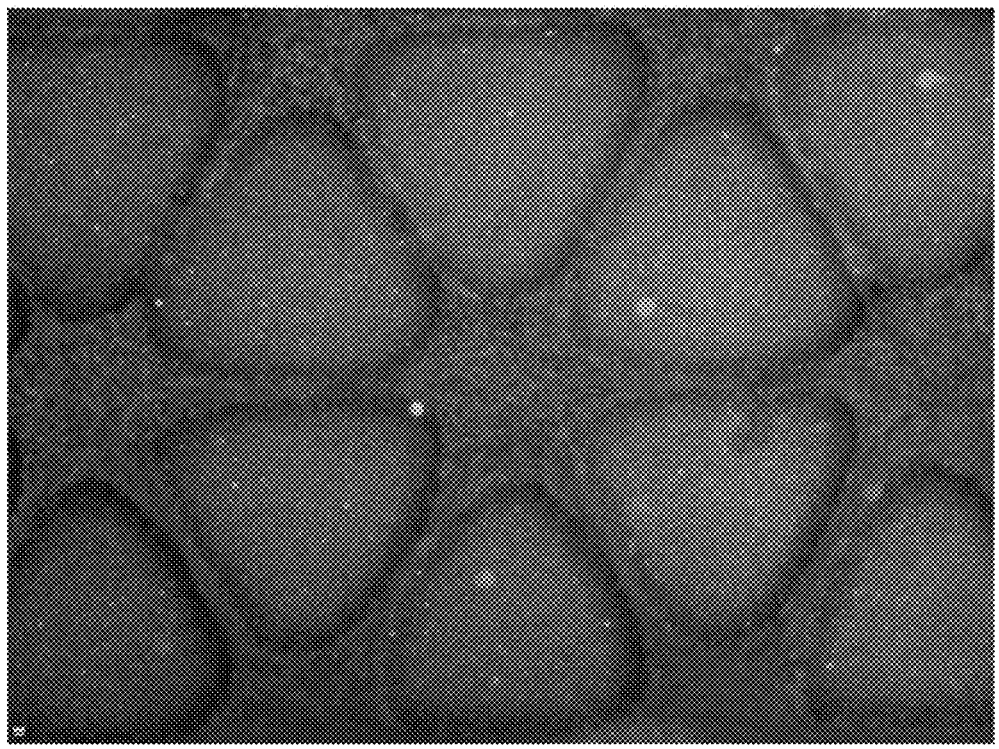
FIG. 5 presents a microfluidic device which comprises multiple microtissues that are interconnected with a perfusion system in order to replicate the vascularization observed in native tissue.

While the examples present an exemplary embodiment of a cardiac-based microfluidic device, additional microtissue specific microfluidic devices have been created. For example, liver, cancer, and skeletal muscle-based microfluidic devices have been fabricated using the same fabrication methods (or with slight modifications) presented herein for cardiac-based microfluidic devices. Thus, the methods presented herein are generally applicable for making any number of tissue-specific microfluidic devices, including microfluidic devices comprising: cells or microtissues from the digestive system, cells or microtissues from the musculoskeletal system, cells or microtissues from the respiratory system, cells or microtissues from the urinary system, cells or microtissues from the reproductive system, cells or microtissues from the endocrine system, cells or microtissues from the cardiovascular system, cells or microtissues from the lymphatic system, cells or microtissues from the nervous system, and cells or microtissues from the integumentary system. It should be understood, that any of the foregoing microtissues can be selected to model or replicate normal tissue in a subject, or alternatively can be used to model or replicate abnormal tissue or diseased tissue. Additionally, the disclosure further provides for microfluidic device which comprises multiple microtissues that are interconnected by perfusion systems to replicate the vascularization observed in native tissue (see FIG. 5).

The cells and microtissues using in the method and devices of the disclosure comprise tissue specific parenchymal cells and may (and typically) include stromal cells. As used herein "stromal cells," generally refer to fibroblasts with or without other cells and/or elements found in loose connective tissue, including but not limited to, endothelial cells, pericytes, macrophages, monocytes, plasma cells, mast cells, adipocytes, etc. As used herein "parenchymal cells," refer to tissue-specific cells, i.e., the cells which form the essential and distinctive tissue of an organ as distinguished from its supportive framework. Parenchymal cells include, but are not limited to, hepatocytes, renal cells, neurons, myocytes etc.

The methods and devices of the disclosure can also be used to study stem cell differentiation and de-differentiation. The term "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew its line or to produce progeny cells which will differentiate into fibroblasts or a lineage-committed progenitor cell and its progeny, which is capable of self-renewal and is capable of differentiating into a parenchymal cell type. Unlike pluripotent stem cells, lineage-committed progenitor cells are generally considered to be incapable of giving rise to numerous cell types that phenotypically differ from each other. Instead, they give rise to one or possibly two lineage-committed cell types.

Figure 3:
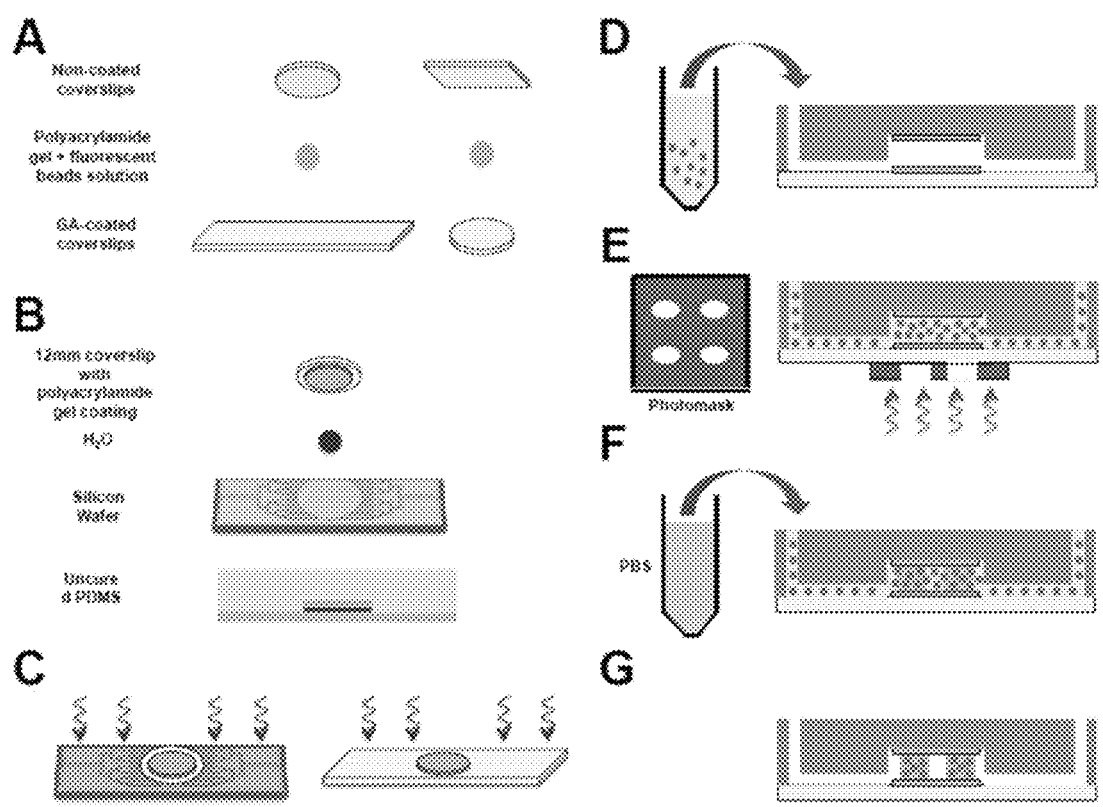
FIG. 3A-G demonstrates an embodiment of the fabrication of 3D micro-tissues within a microfluidic device. (A) Two polyacrylamide (PAm) hydrogels are polymerized by sandwiching the precursor solution mixed with fluorescent particles between a regular and glutaraldehyde (GA)-treated coverslips. (B) A small droplet of deionized water is deposited onto a Teflon coated silicon wafer prior to placing a PAm hydrogel tethered on a circular coverslip. Polydimethylsiloxane (PDMS) solution containing the catalyst is gently poured onto the construct and cured at 37° C. overnight. (C) The PDMS mold attached to the PAm hydrogel is removed from the wafer and inlet and outlet ports of the device are generated using a hole punch. This construct was bonded to a rectangular coverslip tethered to a PAm hydrogel using UV/Ozone treatment. Care should be taken to align the two hydrogels during the process. The device is placed within a humidity chamber at 60° C. for an hour prior to moving to a 37° C. chamber overnight. (D) Cells mixed with GelMa, photoinitiator, and ascorbic acid are injected into the chamber. (E) A transparency photomask is placed underneath the PAm hydrogels before exposing the region to UV light. (F) PBS solution is injected into the device to remove GelMa mixture in the non-polymerized region. (G) The device was attached to a syringe pump containing maintenance media to culture the cells encapsulated within patterned GelMa matrices.
Figure 8:
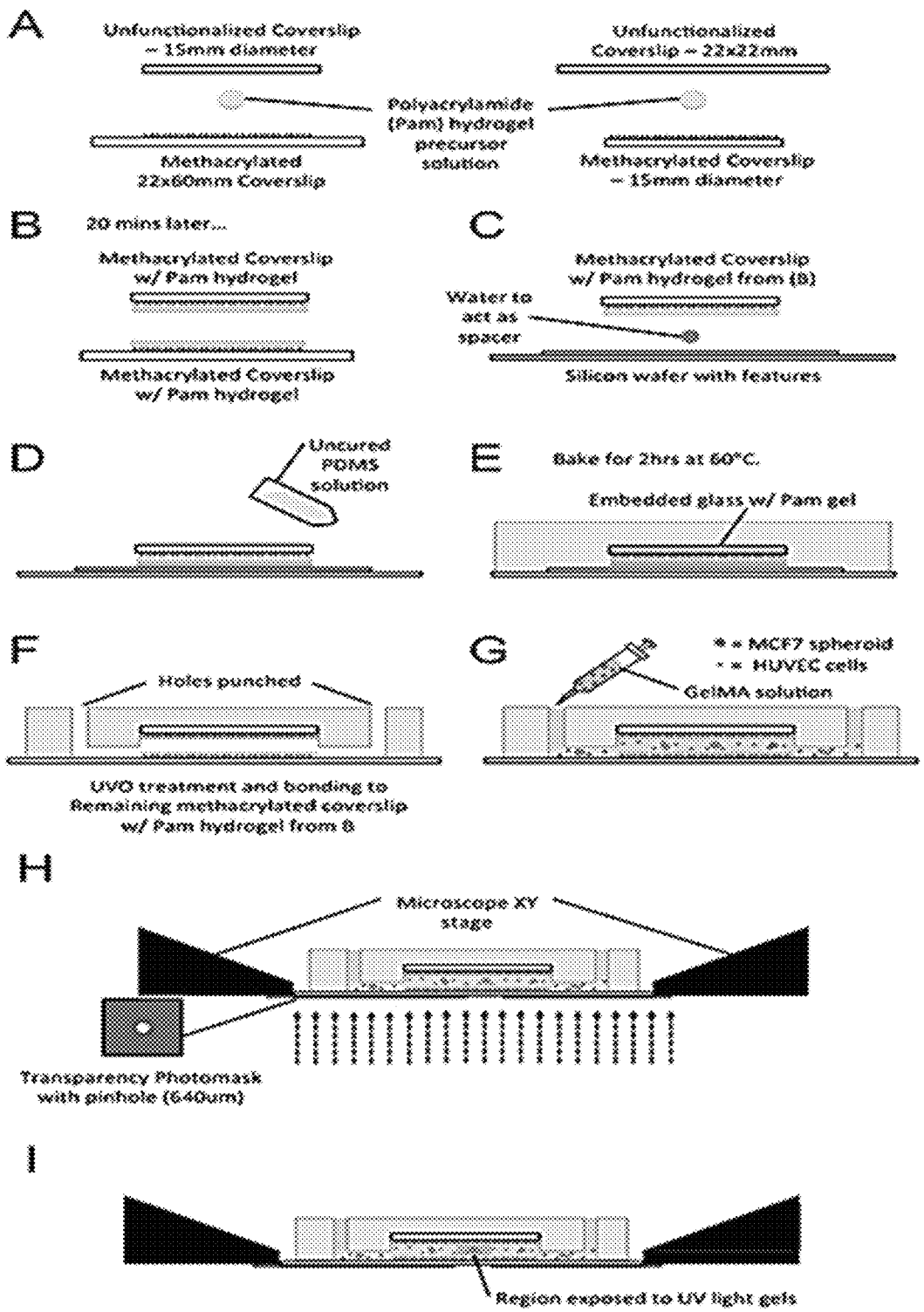
FIG. 8 (Steps A-I) shows a schematic of fabrication of a tumor-on-a-chip devices. (A-B) Synthesis of thin PAm hydrogels tethered to the methacrylated coverslips is done by sandwiching 3 µL of polymer precursor solution between a methacrylated coverslip and a non-treated coverslip. (C-E) 5 µL of deionized water is sandwiched between the Si wafer mold and PAm hydrogel tethered to the methacrylated coverslip to act as a spacer as the uncured PDMS solution is poured on top of the wafer slowly and casted in the oven for 2 hours at 60° C. (F) Holes were punched on the cured PDMS after detachment from the Si wafer prior UVO treatment and bonding. (G) MCF7 spheroids and HUVECs were suspended gently in GelMA solution, drawn into a syringe before injecting into the microfluidic chip. (H-I) The chip is then mounted onto the movable microscope stage mount, on a transparency photomask. This allows us to see the MCF7 spheroids through the photomask on the microscope. After centering a spheroid in the middle of the transparency hole, collimated UV light is reflected via the DAPI filter cube through the transparency, gelling only the selected region of within the microfluidic chamber.

The disclosure further provides methods for fabricating the microfluidic device of the disclosure. In a certain embodiment, the fabrication method comprises polymerizing a first hydrogel precursor solution containing a chemical initiator and optionally fluorescent particles onto surface of a first substrate and polymerizing a first hydrogel precursor solution containing a chemical initiator and optionally fluorescent particles onto surface of a second substrate that have been chemically activated with glutaraldehyde or methacrylate, in order to form a first hydrogel on the first substrate and second hydrogel on the second substrate. For this polymerization step, the polymerized hydrogel should be relatively thin, but can have any shape. Additionally, the first substrate and second substrate generally should be thin and/or transparent, such as glass cover slips, or other clear polymer or inorganic material, preferably that is biocompatible or can be treated to be biocompatible. The method is depicted in FIGS. 3 and 8. For example in FIG. 3A, circular hydrogels of 12 mm diameter were polymerized onto a first substrate of a 12 mm round cover slip and in the middle of a second substrate comprising a long rectangular coverslip. In another embodiment, the fabrication method comprises the step of forming a polydimethylsiloxane (PDMS) mold comprising the hydrogel of the first substrate. As shown in FIG. 3B, water is pipetted (such as 4.0 μL of deionized $H_2O$) onto the chamber on the etched silicon wafer, prior to placing the first substrate comprising the first hydrogel on top of the water droplet. A ratio (e.g., 10:1) of base to curing agent of polydimethylsiloxane (PDMS) (Sylgard 184 elastomer—Dow Corning) is degassed and gently poured over the wafer and coverslip, and then incubated overnight at 37° C. for curing. The PDMS mold is then detached from the wafer and should now contain the first substrate comprising the first hydrogel, with the hydrogel side exposed. The PDMS is then punctured to provide inlet and outlet flow paths. In yet another embodiment, the fabrication method comprises the step of treating the second substrate comprising the second hydrogel and the PDMS mold comprising the first hydrogel to UV-Ozone (e.g., see FIG. 3C). The PDMS mold comprising the first hydrogel and the substrate comprising the second hydrogel are protected from excessive UV irradiation by covering the gels with a 12 mm coverslip coated with dark ink. The depression within the PDMS mold is aligned with the second hydrogel on the second substrate and pressed into contact. In a further embodiment, the fabrication method comprises the step of bonding the PDMS mold to the second substrate at an elevated temperature (e.g., at 37° C. for overnight) to form a fluidics chamber, wherein the bond is chemically and irreversibly formed (e.g., see FIG. 3D). During this process, the inlet and outlet openings of the fluidics device are sealed, for example, with tape to prevent the dehydration of the hydrogels within the device. In another embodiment, the fabrication method comprises the step of equilibrating the first and second hydrogel to physiological pH and osmolarity by using a buffered solution (e.g., phosphate buffered solution). In yet another embodiment, the fabrication method comprises the step of introducing a second hydrogel precursor solution containing a photoinitiator and suspended cells into the fluidics chamber. In a particular embodiment, the fabrication method comprises the step of forming a patterned hydrogel comprising cells by using a photomask which is placed under the fluidics chamber of the device, and a UV light of wavelength 365±40 nm is shone from underneath to contact the photoinitiator and polymerize the hydrogel. This can be repeated numerous times to create a pattern of evenly or non-evenly spaced polymerized islands. The regions of the second hydrogel precursor solution exposed to UV light will polymerize rapidly, thereby forming a patterned hydrogel with cells encapsulated within (e.g., see FIG. 3E). In another embodiment, the fabrication method comprises the step of removing excess unreacted hydrogel precursor solution from the fluidics chamber by washing with a buffered solution (e.g., see FIG. 3F). Thus, a microfluidic device comprising a patterned hydrogel with embedded cells located between the first and second hydrogel is created, a ("gel-on-gel sandwich") (e.g., see FIG. 3G). A second set or type of cell can also be added following the polymerization process of the first "islands". The polymerization step can be repeated to provide a second set of patterned cellular islands. In this way, microtissue of different cellular compositions can be generated, using polymerized hydrogel islands of different cellular composition, spaced in such a way as to mirror in vivo tissue organization. The cells of the microfluidic device can be kept alive by introducing cell culture media and maintaining the cells under standard cell culture conditions (i.e., 37° C. and 10% $CO_2$).

Moreover, the cellular islands can be exposed to chemico- and/or physical strains to modify their morphology and study cell-cell interactions and cellular communication. The methods and compositions also allow for screening of the cells to natural and man-made chemical agents (e.g., chemotherapeutics and drugs). In some embodiments, the cells are exposed to fluid flow strains (i.e., stress/shear strains).

The cells may be genetically engineered for expression of a certain polypeptide or nucleic acid. The genetically engineered cells can constitutively produce express the nucleic acid or polypeptide or can be induced by contacting them with an inducing agent that promotes expression. In this way the system can be used as a production system for obtaining the expressed polypeptide or nucleic acid.

In a particular embodiment, a microfluidic device disclosed herein comprises a patterned gelatin-methacrylate (GelMa) hydrogel comprising cells placed between two polyacrylamide (Pam) hydrogels, a ceiling and floor hydrogel, which are attached to the top and bottom surfaces of the fluidics chamber. In some embodiments, the GelMa cell containing hydrogels comprise parenchymal cells and stromal cells. In a further embodiment, the cells are cardiomyocytes, cancer cells, and/or endothelial cells.

In yet another embodiment, a microfluidics device disclosed herein comprises ceiling and floor hydrogels that have the same rigidity (e.g., about 10 kPa) and thickness (e.g., about 150 μm). Hydrogels having the same rigidity and thickness eliminates the possibility of mechanical edge effects on the cells caused by fixing the patterned hydrogel to a rigid glass surface. In an alternate embodiment, the floor and ceiling hydrogels can be chosen to have different rigidities and/or thicknesses.

In another embodiment, the contraction profile of cardiomyocytes can be quantified by analyzing the forces transmitted from the patterned hydrogel into the floor and ceiling hydrogels. The traction stresses within the floor and ceiling hydrogels (i.e., inert hydrogels) can be calculated so as to circumvent the inaccuracies in measurements associated with cell induced ECM remodeling of the patterned hydrogel.

In further embodiments, the disclosure provides that a microfluidic device disclosed herein can be used to test responsiveness of cells or microtissues to drugs or other biological agents. Accordingly, the microfluidic devices of the disclosure can be used as effective in vitro testing platforms for small molecules. For example, in embodiments presented herein, it was shown that the residual stresses cardiac-based microtissues were modulated by the presence of epinephrine. The effect of epinephrine was studied by analyzing the difference in contraction frequency and contractile force generated by a microtissue in the presence and absence of each small molecule. The increased magnitude and frequency of contraction with the addition of epinephrine (0.1 µg/mL) proved the utility of this system for studying the cardiac-specific effect of pharmaceuticals. Further, the ability to visualize these effects and take contractile force measurements in real-time provides for systems that can determine both immediate and long-term drug effects up to 14 days. These capabilities make the microfluidic devices disclosed herein especially attractive for drug screening as it addresses shortcomings of current models. Specifically, real-time analysis cannot be performed in animal model testing while current organ-on-chip systems lack real-time force readout.

The microfluidic devices disclosed herein can be used for many translational applications in healthcare. The systems of the disclosure afford cellular spatial arrangement along with the ability to work with multiple cell types. For example, the encapsulation of human vascular endothelial cells (HUVECs) in a geometry resembling the human circulatory system between the cardiac microtissues would create a flow system with 3D vascularized cardiac microtissues, recapitulating the in vivo environment even more closely. Moreover, with the incorporation of cardiomyocytes derived from human-induced pluripotent stem cells (hiPSCs), can potentially predict human-specific drug responses much more accurately than current pre-clinical methods that rely on 2D monolayer and animal model testing. Further, fabricating the microfluidic 3D chip systems with hiPSCs opens the door for personalized drug testing to assess patient-specific responses to certain pharmaceuticals since hiPSCs can be generated using a patient's own adult cells. Additionally, by modeling cardiomyopathies and other cardiac conditions within the microfluidic 3D chip systems, the systems can recapitulate disease states in a 3D flow based system.

The microfluidic device of the disclosure is particularly amendable as in vitro system to study the response of cells and/or tissues to physical, electrical, chemical, and/or mechanical changes in the environment. One such application is the use of these systems to survey and/or assay the chemical, electrical, and mechanical response of single cells and/or tissues to natural or synthetic chemical or biological agents, such as pharmaceutical drugs which are currently in development and which have an unproven hypothesis of their in vivo effect. Pharmaceutical drugs can be infused into the system at various experimental dosages and the responses of the tissue can be determined. For example, by using the drug epinephrine, the microfluidic device comprising cardiac-microtissues beat at a higher frequency than without epinephrine. Moreover, measurements of the physical and temporal changes exerted by these cardiac-microtissues were quantifiable. Further, one or more microfluidic devices comprising multiple microtissues can be connected together to create an organ system to measure the response of different tissues to the same drug. The microfluidic devices of the disclosure can shorten the drug testing timeline, ultimately reducing the overall cost to bring a drug to market.

Additionally, microfluidic devices comprising iPSCs allow for the creation of microtissues with cells that bear genetic traits for diseases or abnormal conditions, allowing for modeling of specific diseases and their progression. Microfluidic devices comprising iPSCs or other cells from a patient can allow for optimization of drug therapy for the patient by testing drug regimens with microfluidic devices. For example, microfluidic devices comprising patient-specific cancer cells can be grown into a tumor within the device and subjecting it to different cancer drugs to determine the optimal therapy for that patient.

Although the platform described here is exemplified using endothelial and cancer cell co-cultures, the platform and approach described herein provides a versatile framework for establishing systems with increased complexity observed in physiological systems including various tumors. In vivo tumor microenvironments are comprised of a variety of resident cells ranging from stromal cells to immune cells. The incorporation of supporting cells into the device can be accomplished by incorporating these cells into the GelMA structures along with HUVECs and cancer spheroid. The 3D pattern mediated confinement of cells within the device allows the compartmentalization of various cell populations to dissect the interaction and contribution of various cellular populations towards cancer growth individually and in concert. Such an in vitro platform recapitulating various attributes of in vivo tumor microenvironment could not only offers new insights but could also be used as a drug-screening platform. The presence of an encompassing endothelium closely mimics the vasculature present within actual tumors by allowing the circulating cells to attach, roll, and transmigrate. This could provide an additional perspective for analyzing the extravasation of circulating cells into the tumor site, which can be achieved by introducing suspended single cells into the injected media or intravasation of cancer cells into the circulating system.

This disclosure also provides the development of a tumor-on-a-chip platform comprised of cancer spheroid encapsulated within a GelMA hydrogel and surrounded by an endothelial barrier. Using a single step process, HUVECs and MCF7 spheroids were encapsulated within the device. In addition, the differential chemoattractant-induced motility of HUVECs and cancer spheroids was used to control their confinement and organization within the device. The data show the effect of flow rates on the generation of concentration gradient of soluble factors within the cell-laden GelMA structures.

Within the GelMA hydrogel containing both HUVECs and MCF7 spheroids, the cancer cells did not migrate in response to the gradient of soluble factors as they were confined to the center of the hydrogel. This lack of motility could be attributed to insufficient strength of the chemotactic gradient to cause the migration of cancer spheroids and/or cancer cells from the spheroids. In addition, the cell-cell contact mediated by the cadherin junctions within the cancer spheroid may also mitigate migration of cancer cells away from the spheres and within the GelMA hydrogel.

The Doxorubicin studies showed the potential of this tumor-on-a-chip platform to assess the response of cells to oncologic drugs. The penetration of Doxorubicin into the tumor spheroid and its quantifiable cytotoxic effect on the cancer spheroid were assessed. Additionally, the loss of the endothelial barrier in devices exposed to high doses of Doxorubicin (>10 μg/mL) suggests the lack of target specificity of this oncologic drug.

This tumor-on-a-chip device can be translated to assess the efficacy of other cancer therapeutics in a physiologically relevant system that provides a co-culture system to test drug specificity, cancer spheroid in a 3-D environment, as well as an endothelial barrier that can potentially resist drug penetration especially for higher MW compounds.

The following examples are intended to illustrate but not limit the disclosure. While they are typical of those that might be used, other procedures known to those skilled in the art may alternatively be used.

EXAMPLES

Cell Culture.

MCF7 and HUVECs were obtained from ATCC. MCF7 cells were cultured in growth media (GM) comprised of Dulbecco Modified Eagle's high glucose media (Hyclone), 10% fetal bovine serum (FBS, Gibco), and 1% Penicillin/Streptomycin (Gibco). HUVECs were cultured in HUVEC Media (HM) containing 79% M199 media (Gibco), 10% FBS (Gibco), 10% endothelial cell growth media (Cell Application, Inc.), and 1% Penicillin/Streptomycin. HUVECs used in this study were limited to cells between passage 6 and 8.

MCF7 Spheroid Formation.

MCF7 cells were cultured to about 80% confluency prior to trypsinization. To create spheroids, 1 million MCF7 cells in 4 mL GM were plated in a 60 mm diameter petri dish and cultured on an orbital shaker (VWR, Model No. DS-500E) at 45 rpm in a humidified incubator maintained at 37° C. and 5% $CO_2$. The cultures were maintained for ~20 hours to form spheroids. The average diameter of the spheroids were found to be ~200 μm.

Synthesis of lithium phenyl-2,4,6-trimethylbenoylphosphinate (LAP):

First, 2,4,6-trimethylbenzoyl chloride was mixed drop-by-drop with an equal molar solution of dimethyl phenylphosphonite under argon while stirring at room temperature. After 18 hours, the temperature of the reaction mixture was increased to 50° C. Then, lithium bromide mixed with 2-butanone was added to the reaction mixture in excess, causing precipitation within 10 minutes. After precipitation, the temperature was again cooled to room temperature and left for 4 hours. Next, to ensure complete removal of excess lithium bromide, the precipitate was collected by filtration and washed three times using 2-butanone. Finally, the product was dried in vacuo to remove excess 2-butanone, yielding lithium phenyl-2,4,6-trimethylbenoylphosphinate (LAP).

Synthesis and Purification of PEGDA:

Poly(ethylene glycol)-diacrylate (PEGDA) was prepared as described by Kang et al., (*Journal of materials chemistry B, Materials for biology and medicine* 2:5676 (2014)). Briefly, 5.29 mmol of poly (ethylene glycol) (18 g of 3.4 kDa; Sigma Aldrich) was dissolved in 300 mL of toluene at 127° C. and kept under reflux for 4 hours with vigorous stirring. To remove trace amounts of water, the solution was subjected to azeotropic distillation. Anhydrous dichloromethane (180 mL) was added at room temperature, and subsequently, 1.623 mL (11.64 mmol, 2.2 equivalents) of triethylamine was added under vigorous stirring. The reaction mixture was transferred to an ice bath to further cool it down. Upon cooling, 0.942 mL (11.64 mmol, 2.2 equivalents) of acryloyl chloride mixed in anhydrous dichloromethane (15 mL) was introduced dropwise to the mixture at 4° C. over 30 minutes. The reaction was kept for 30 more minutes at 4° C. before increasing to 45° C. overnight. The reaction mixture was filtered through diatomaceous earth to remove quaternary ammonium salts. The filtrate was concentrated using a rotary evaporator and precipitated in excess diethyl ether. The precipitated product was re-dissolved in dichloromethane and re-precipitated in diethyl ether. The resultant PEGDA was filtered and dried under vacuum at room temperature for 24 hours. The dried PEGDA was further purified using a Sephadex G-25 column (GE Healthcare Life Sciences) and lyophilized.

Fabrication of Silicon Mold.

Microfluidic channels were photolithographically defined using NR9-1500PY negative photoresist (Futurrex, Frankling, N.J., USA) on a 4-inch diameter Si wafer. The Si wafer with the photoresist defined was then etched using the deep reactive ion etching (DRIE) process. In the DRIE process, SF6 gas was flowed at 100 sccm throughout the 11 seconds of reaction time, followed by a passivation cycle when C4F8 gas was flowed at 80 sccm for 7 s. A 75 μm of etching depth was achieved under the etching rate of about 0.7 μm per cycle. After the DRIE process, the NR9-1500PY photoresist was removed by immersing in acetone for 4 hours before rinsing with methanol, isopropanol, and deionized water. The Si mold was then dried under compressed nitrogen gas and silanized by vapor deposition of trichlorosilane (TCI Inc, Portland, Oreg., USA) to facilitate PDMS molding and removal.

Methacrylation of Glass Coverslips.

Glass coverslips (15 mm diameter) were treated with 2.5 M NaOH solution for 30 minutes before rinsing in DI water and air drying. A dilute solution of glacial acetic acid was prepared in DI water at a ratio of 1:10. A working solution containing 200 μL of ethanol, 1 μL of 3-(trimethoxysilyl) propylmethacrylate (Sigma Aldrich), and 6 μL of the diluted acetic acid was prepared. The cleaned glass surfaces were treated with this solution for 6 to 10 minutes prior to rinsing with pure ethanol for 10 minutes. The coverslips were dried under airflow and incubated in 60° C. for 2 hours. The coverslips were used within 24 hours.

PLL-PEG Coated Coverslips.

12 mm or 15 mm diameter coverslips, or 22×22 mm square coverslips were treated with 100% ethanol for 15 minutes and dried under gentle airflow. The cleaned glass surfaces were exposed to UV/Ozone for 6 minutes and were immediately treated with 0.1 mg/mL PLL-PEG (Surface Solutions), diluted in PBS from a stock solution with concentration of 5 mg/mL. After 30 minutes of PLL-PEG treatment, the coverslips were rinsed in distilled water and were dried through aspiration. PLL-PEG coated coverslips were used within 24 hours.

Synthesis and Purification of Gelatin-Methacrylic (GelMa):

Bovine skin gelatin (10 g; Sigma-Aldrich, St. Louis, Mo., USA) was mixed at 10% (w/v) with phosphate buffered saline (PBS) (100 mL; Gibco, Billings, Mont., USA) and stirred at 60° C. until fully dissolved. Next, methacrylic anhydride (MA) (Sigma Aldrich, St. Louis, Mo., USA) was added to the solution at a rate of 0.5 mL/min for a total of 8 mL. The solution was then stirred for 60 minutes at 50 C. After being diluted 2× with warm PBS, the solution was dialyzed against distilled water using 12-14 kDa cutoff dialysis tubing (Spectrum Laboratories, CA, USA) for one week (3 times/day water change) at 40° C. in order to remove the unreacted methacrylic anhydride and methacrylic acid from the solution. Next, the GelMA solution was frozen using liquid nitrogen and lyophilized in a freeze dryer for 4 days before being stored at −80° C. until usage. The dried GelMA was further purified using column chromatography with a Sephadex G-25 column (GE Healthcare Life Sciences) and then lyophilized.

Embedded 3D Patterning:

A known weight of GelMA powder was added into a known volume of PBS to create 10% (w/v) solution. The GelMA in PBS solution was vortexed at room temperature to dissolve the polymer. The resultant mixture was transferred to a 60° C. water bath for 15 minutes and vortexed for an additional minute at room temperature. This process was repeated once more to achieve complete dissolution of the GelMA in PBS. Once completely dissolved, the solution was brought to 37° C. and used to create acellular and cell-laden hydrogel structures.

The 10% (w/v) GelMA solution was supplemented with the photoinitator LAP and 200 nm diameter green fluorescent particles at concentrations of 2 mM and 1% wt/v, respectively. In the case of cell-laden, for cellular constructs, ~0.01% ascorbic acid was used in the GelMA solution. A 22×22 mm square coverslip was cleaned in DI water and dried prior to adding the precursor solution onto the surface. A PLL-PEG treated 12 mm coverslip was gently placed on top to sandwich the solution between the two glass surfaces.

A transparency photomask containing dark background and clear patterns was placed onto the microscope stage and positioned under bright field such that the desired pattern is centered over the eyepiece. The GelMA construct was placed onto the mask and photopolymerized using a collimated UV light source, which was generated by passing the light from an X-Cite Mercury lamp through a conventional DAPI channel filter cube with excitation and emission, around 358 nm and 463 nm, respectively. The gelled construct was transferred to a petri dish filled with 37° C. PBS and the solution was pipetted gently yet repeatedly between the glass coverslips to remove the unpolymerized GelMA solution and detach the PLL-PEG treated coverslip. The resulting GelMA structures were temporarily stored within a PBS solution.

PEGDA (Mn: 3400) was dissolved in PBS to achieve 10% wt/v along with 2 mM LAP and 1% wt/v of 200 nm diameter red fluorescent particles. The GelMA structures attached to the square coverslips were retrieved and the excess liquid was aspirated prior to the addition of the PEGDA precursor solution onto the GelMA patterns. A 15 mm diameter methacrylated coverslip was gently placed on top and the construct was polymerized as previously described. The coverslip was transferred into a PBS solution afterwards and the gelled construct tethered onto a methacrylated coverslip was retrieved. The hydrogel composite structure was temporarily stored within a PBS solution.

To complete the enclosure of the GelMA features within the PEGDA hydrogel, PEGDA precursor solution was aliquoted onto a 22×22 mm square coverslip. The patterned construct was retrieved and the excess liquid was removed prior to placing the hydrogel surface onto the precursor solution. After photopolymerization and removal of the cover slip, the supported 3D constructs tethered onto 15 mm diameter coverslips were obtained.

Free-Standing Photo-Patterned Scaffolds:

The GelMA patterns were constructed on 22×22 mm square coverslips and were incubated in PBS as described above. PEGDA was dissolved in PBS to obtain a solution containing 10, 20, or 30% w/v along with LAP (concentration of 2 mM). The coverslips containing the patterns were removed from PBS and the excess liquid was aspirated. The PEGDA solution was added onto the patterns and a 15 mm diameter PLL-PEG coated coverslip was placed on top. The precursor solution was photopolymerized and the resulting gel was incubated in PBS for 5 minutes at room temperature. The PLL-PEG coated coverslip was mechanically removed. The GelMA construct remaining on the square coverslip was carefully detached to yield a free-standing scaffold.

Multi-Layered Scaffolds:

To create the first layer of the scaffold, 22×22 mm square coverslips were coated with PLL-PEG while the 15 mm diameter circular coverslips were methacrylated. This resulted in GelMA structures covalently bonded to the circular coverslip. GelMA precursor solution supplemented with 2 mM LAP was added onto the PLL-PEG coated square coverslip prior to placing the circular coverslip on to the solution submerging the GelMA features. The construct was photopolymerized and the circular coverslip was removed. The above process was repeated to construct supporting layers and additional patterned layers.

Fabrication of Tumor-On-a-Chip Device.

The device includes a trilayer hydrogel system where cell-laden GelMA hydrogels were sandwiched between two polyacrylamide (PAm) hydrogels. The fabrication of the device involves the following:

(A) Methacrylation of Glass Surfaces:

To achieve the chemical tethering of PAm hydrogels, glass coverslips were methacrylated as described above. Briefly, glass coverslips were cleaned with 1.5 M NaOH for 30 minutes followed by rinsing with DI water and drying with air. The cleaned coverslips were treated with 2% (v/v) 3-(Trimethoxysilyl)-propyl methacrylate solution diluted in 0.54% glacial acetic acid and 99.46% ethanol for 5 minutes at room temperature to immobilize methacrylate groups onto the surfaces. Care was taken to aliquot sufficient volume of the reacting solution onto the coverslips to eliminate artifacts associated with their evaporation. The surface modified coverslips were washed with pure ethanol for 10 minutes under gentle stirring to remove excess reactants. The above step was repeated twice, rinsed with DI water, and dried at 50° C. for 30 minutes. The coverslips were used immediately.

(B) Trilayer Hydrogel Formation:

Methacrylated coverslips of 22×60 mm rectangular and 15 mm diameter were used. 3 µL of a polyacrylamide hydrogel precursor solution comprised of 5% (w/v) acrylamide (Am), 0.2% (w/v) Bis-Acrylamide (BisAm), 0.1% (w/v) Ammonium Persulfate (APS), and 0.01% (w/v) N,N,N',N'-Tetramethylethylenediamine (Sigma-Aldrich) in PBS, was placed in the center of the methacrylated 22×60 mm rectangular coverslip and the droplet was covered with a non-methacrylated 15 mm diameter coverslip. This would result in the bottom layer of the device (FIG. 8 step A, B). This process was repeated with a methacrylated 15 mm circular coverslip and non-methacrylated square coverslip to fabricate the top layer (FIG. 8 step A-B). The precursor solution was left to polymerize for 20 minutes prior to gently removing the non-methacrylated coverslips. The resulting structures containing PAm hydrogels tethered to the circular and rectangular coverslips were allowed to equilibrate in PBS overnight at room temperature to remove trace amounts of unreacted monomers.

Around 5 µL of DI water was placed onto a circular region of the fabricated silicon mold before covering the droplet with PAm hydrogel tethered-15 mm diameter circular coverslip (FIG. 8 step C). Polydimethylsiloxane (PDMS, Sylgard 184) base solution was mixed with its curing agent at a weight ratio of 10:1 and degassed to remove air bubbles if any (FIG. 8 step D). This mixture was gently poured onto the silicon wafer containing the PAm hydrogel and baked at 60° C. for 2 hours (FIG. 8 step E). The PDMS mold containing the hydrogel was detached from the silicon wafer and bonded to the rectangular coverslips containing a PAm hydrogel using UV-Ozone treatment (FIG. 8 step F). Care was taken to prevent direct exposure of the PAm hydrogel to deep UV.

The PDMS mold and the glass coverslips were immediately attached to each other while maintaining the alignment between the hydrogels on their respective surfaces. This ensures that the top and bottom of the microfluidics chamber are comprised of PAm hydrogels. The fabrication process was completed by bonding the PDMS mold and glass coverslips at 60° C. The device was equilibrated in PBS and UV sterilized for 45 minutes prior to using it for cell culture.

(C) Preparation of GelMA Solution.

Gelatin methacrylate was dissolved in PBS to achieve a 10% wt/v precursor solution. To ensure complete dissolution, the GelMA dispersed PBS was incubated at 60° C. in a water bath for 20 minutes. The GelMA solution was syringe filtered (pore size of 0.22 µm) to remove any insoluble residues and maintained at 37° C. until use.

(D) Encapsulation of Cells within GelMA Structures in Microfluidic Device.

HUVECs and MCF7 spheroids were encapsulated within GelMA hydrogels. The MCF spheroids were passed through a cell strainer having 100 µm pore size (Corning) to eliminate single cells and small spheroids. Around 50 spheroids with a diameter of ~200 µm were dispersed in 5 mL of PBS containing 2 million HUVEC cells. The mixture was centrifuged for 3 minutes at 800 rpm. The supernatant was aspirated and 100 µL of 10% GelMA solution was added to the cell pellet. The cells were re-suspended gently using a pipette before the addition of 0.01% ascorbic acid (antioxidant) and 2 µM LAP (photoinitiator) to the solution. This solution was again mixed gently, drawn into a syringe, and injected into the microfluidic device (FIG. 8, step G).

This device was placed onto a transparency film photomask containing an ellipse pattern and mounted onto a microscope stage (FIG. 8, steps H-I). Using the stage controller of the microscope, the position of the fluidic device was moved to locate individual MCF7 spheroids surrounded by HUVECs under bright field illumination. Each location was exposed to UV light with an excitation and emission wavelengths of approximately 358 and 463 nm, respectively, for 18 seconds. Several locations were photopolymerized before flushing the device with PBS containing 4% Penicillin/Streptomycin. Mixed Media (MM) containing 50% GM and 50% HM was subsequently injected into the device and the GelMA structures containing MCF7 spheroids and HUVECs were cultured at 37° C. and 10% $CO_2$.

Cell Culture and Encapsulation:

Human mesenchymal stem cells (hMSCs) and human fibroblasts were cultured in growth medium comprised of 1% Penicillin/streptomycin, 1% L-Glutamine, 10% Fetal Bovine Serum (Gibco), and 88% DMEM (HyClone®, Thermo Scientific). Human umbilical vein endothelial cells (HUVECs) were cultured in medium composed of 1% Sodium Pyruvate (Life Technologies), 1% Penicillin/Streptomycin, 10% Fetal Bovine Serum (Gibco), 10% Endothelial Cell Growth Medium (Gibco) and 78% M199 (Gibco).

To label the cells, they were trypsinized and resuspended in 7 µM green or red cytotracker dye or 1 µg/mL of Hoescht 33342 (Life Technologies) dissolved in OPTIMEM (Gibco). After 20 minutes of incubation, the cells were washed multiple times with PBS.

During the cell encapsulation, a cell pellet was resuspended in 10% GelMA precursor solution supplemented with 2 mM LAP and 0.01% ascorbic acid. The cells were patterned following the procedure discussed in above, until the step where cell-laden GelMA patterns were embedded with an additional hydrogel layer. The cell-laden constructs were incubated in sterile PBS containing 2% Pen/Strep for 5 minutes at 37° C. prior to replacing the solution with hMSC growth medium.

Synthesis of Polyacrylamide (Pam) Hydrogels:

Round glass coverslips (12 mm) and rectangular glass coverslips (24×50 mm) were first cleaned by treatment with 2.5 M NaOH for 20 minutes, rinsed with deionized water and then air dried. A silane solution was applied to the coverslips for 5 minutes to chemically functionalize the glass. After rinsing and drying the coverslips, a 0.75% glutaraldehyde solution was applied for 30 minutes followed. The treated coverslips were then rinsed and dried prior to application of the hydrogels.

Polyacrylamide (PAm) hydrogels were synthesized by mixing together 40% acrylamide solution (6.25 µL), a 2% bisacrylamide solution (5.625 µL), and PBS (37.25 µL). Fluorescent green beads were added to this solution (50 µL) at a 1:100 dilution. Ammonium persulfate (APS) (0.6 µL) was then added from a 10% wt/vol stock solution. Immediately prior to polymerization, tetramethylethylenediamine (TEMED) was added to the PAm solution (0.6 µL). The PAm solution (4 µL) was applied to a new 22×22 mm square glass coverslip and sandwiched with a glutaraldehyde treated 12 mm round coverslip, while another aliquot of the PAm solution (4 µL) was applied to a glutaraldehyde treated 24×50 rectangular coverslip and sandwiched with a new, untreated 12 mm round coverslip. These were placed in a humidity chamber and allowed to polymerize for 20 minutes. A razor blade was then used to clip the two coverslips apart. The PAm-coated glass was kept hydrated in water to preserve the PAm until further use.

Embedded 3D Patterning:

The GelMA solutions supplemented with LAP and fluorescent particles were sandwiched between PLL-PEG treated and regular coverslips (see FIG. 1A), which was exposed to a collimated UV light through a photomask printed with the desired patterns. The PLL-PEG treatment was used to promote adhesion of the hydrogel onto the regular coverslip. The non-irradiated regions were then washed off to leave behind the 3D patterned GelMA structures (see FIG. 1B). To embed the 3D patterned structures within a hydrogel, the GelMA structures formed onto the glass coverslip was immersed within PEGDA solution containing LAP and photopolymerized, where the PEGDA solution was sandwiched between the GelMA layer and a methacrylated glass coverslip prior to gelation (see FIG. 1C). The use of methacrylated coverslip ensures the detachment of the GelMA structures after they are embedded within the PEGDA hydrogels. To achieve the complete embedment of the GelMA structures, the above-mentioned procedure was repeated using a glass coverslip that was not methacrylated (see FIG. 1D). Though the results described here utilize PEGDA to create the surrounding layer, any photopolymerizable biomaterials could be used.

Figure 2:
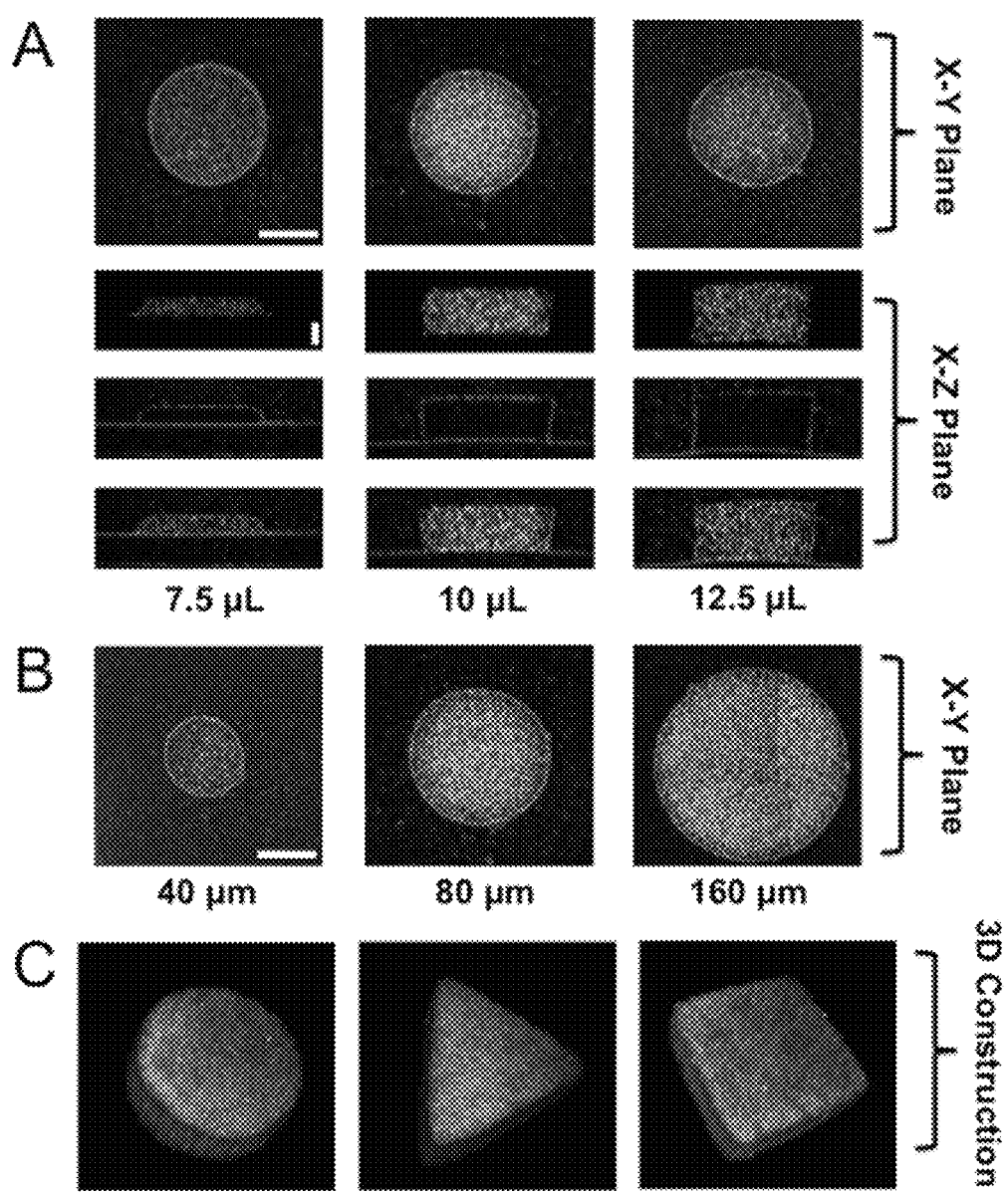
FIG. 2A-C demonstrates that the hydrogels can be patterned to have various geometrical features by using a photomask to limit the spatial distribution of UV light. (A) Demonstrates that different cylinder lengths are achievable by using a photomask with the same pattern in combination with varying concentrations of hydrogel polymer solution. (B) Demonstrates that the diameters of the resulting patterned hydrogels can be varied depending upon the selection of photomask. (C) Demonstrates that hydrogels with varying geometries can be generated using the photomask methods.

Varying the Height and Size of the 3D Patterned Structures:

The photo-patterning process described here can easily be used to vary the height and sizes of the patterned structures. The height of the structures are adjustable by varying the volume of GelMA precursor solution sandwiched between the cover slips. By exposing volumes of 8, 14, and 20 μL of GelMA solutions to UV through circular photomask patterns, cylindrical structures were fabricated with heights of approximately 47, 103, and 115 μm, respectively (see FIG. 2A). FIG. 2A depicts the z-stack confocal images of the cylindrical hydrogel structures of different heights. The X-Y cross-sections show the circular GelMA structures, embedded with green fluorescent beads, surrounded by PEGDA hydrogels embedded with red fluorescent beads (see FIG. 2A, Top Panel). The confocal images in X-Z plane show the increase in height of the GelMA structures encased within the PEGDA layer with increase in the volume of the GelMA precursor solution (see FIG. 2A, Bottom Panel). The images of GelMA with green beads and PEGDA with red beads have been merged to demonstrate the embedment of GelMA structures within a PEGDA hydrogel. The size of the structures can be controlled by altering the size of the patterns on the photomasks. FIG. 2B illustrates X-Y cross-sections of the circular structures with increasing diameters of 80, 160, and 250 μm. In addition to circles, other basic geometries have been created such as triangles and squares. The 3D reconstructed images from the z-stack volumes of these structures are depicted in FIG. 2C.

Since the 3D structures are mechanically supported by the PEGDA hydrogels, free-standing scaffolds containing embedded 3D patterned GelMA structures can be generated. By tuning the concentration of the PEGDA hydrogels from 10% to 30%, the mechanical properties of the surrounding hydrogel can be varied. The mechanical properties of the PEGDA hydrogels increase with increasing precursor concentration.

PDMS Solution Preparation for Fluidics Chamber:

Poly(dimethylsiloxane) (Sylgaard 184) was obtained and prepared by mixing a 10:1 ratio by mass of base to curing agent. The solution was thoroughly mixed for 3 minutes prior to it being poured gently on top of a silicon wafer containing PAm-coated 12 mm glass coverslips in a 15 cm petri dish. Once the PDMS was level and an even distribution was achieved, it was degassed in a vacuum chamber for approximately 30 minutes to remove all bubbles. The PDMS was then incubated overnight at 37° C. for curing.

Fabrication of Cardiac-Based Microtissues on a Chip:

Poly-acrylamide (PAm) hydrogels embedded with 200 nm diameter green fluorescent particles were polymerized on glutradehyde-treated rectangular coverslips (12 mm diameter; 24×50 mm) (see FIG. 3A). Next, deionized $H_2O$ (4.0 μL) was first pipetted onto a circular chamber on an etched silicon wafer, prior to placing a hydrogel-tethered round coverslip on top of the water droplet (see FIG. 3B). A 10:1 ratio of base to curing agent of polydimethylsiloxane (PDMS) (Sylgard 184 elastomer—Dow Corning), was degassed and then gently poured over the wafer and coverslip, and incubated overnight at 37° C. for curing. The polymerized PDMS was then detached from the wafer. The PDMS contained the embedded hydrogel-tethered coverslip (with the hydrogel side exposed). The PDMS was then hole punched to provide inlet and outlet flow paths. The PDMS and the rectangular coverslip were then subjected to a UV-Ozone treatment (see FIG. 3C). The hydrogels attached on the PDMS mold and the rectangular coverslips were protected from deep UV by covering the gels with 12 mm coverslips marked with dark ink.

The circular depression within the PDMS was aligned with the hydrogel tethered on the rectangular coverslip and pressed into contact. The resulting composite was incubated overnight at 37° C. to allow the PDMS to chemically and irreversibly bond to the glass, thereby forming the device as depicted in FIG. 3D (minus cells). The inlet and outlet openings of the fluidics device were sealed with tape to prevent the dehydration of the hydrogels within the device. Following bonding, phosphate buffer solution (PBS) was introduced into the chamber on the subsequent day to equilibrate the hydrogel to physiological pH and osmolarity.

Isolated primary neonatal cardiomyocytes were mixed with 8.5% wt/vol GelMa solution containing 0.01% wt/vol of ascorbic acid and 2 mM lithium phenyl-2,4,6-trimethylbenoylphosphinate (LAP). This solution was injected into the fluidics chamber (see FIG. 3D) and a dark transparency mask containing the clear ellipse patterns was placed under the circular chamber of the device. The GelMa solution was photo-polymerized using a UV light source with an excitation wavelength of 365±40 nm (see FIG. 3E). The regions of the hydrogel precursor solution exposed to UV light polymerized rapidly, thereby forming the microtissues with cells encapsulated within (see FIG. 3E). The unreacted hydrogel precursor solution was removed from the fluidics chamber by injecting PBS in excess (see FIG. 3F). Thus, the 3D device with patterned cardiac-microtissues between hydrogels was created (see FIG. 3G). The device was then perfused with cardiomyocyte growth media and incubated at 37° C. and 10% $CO_2$ culture conditions.

Time-Lapse Imaging of Cardiomyocyte Embedded Structures During Contraction:

The contraction of the GelMa structures embedded with cardiomyocytes was imaged using 40× lenses mounted onto a spinning disk confocal microscope. The fluorescent particles at the top surface of the PAm hydrogel below the GelMa structures were acquired at ~20 frames per second for 90 seconds. In order to encompass the entire GelMa structure, three fields of view were acquired. The time-lapse images from these fields of view were temporally synchronized to account for latency in the deformations between each field. These images were then stitched using custom Matlab software to obtain the entire image containing the GelMa structures.

Calculation of Contractile Forces:

To quantify the forces generated by the cardiomyocytes, the propagation of forces originating from the GelMA structures were exploited to PAm hydrogels. Since GelMA is derived from collagen and is susceptible to degradation, the forces cannot be accurately determined from visualization of the GelMA structures due to their labile material properties. However, the inert nature of PAm hydrogels allow for the calculation of forces under the assumption of linearly isotropic material properties. In addition, a measured value of 8.5 kPa was used for the elastic modulus of the PAm hydrogel and 0.45 for Poisson's ratio.

By treating the PAm hydrogel as a 3 dimensional block tethered at the bottom in mechanical equilibrium, a finite element (FE) approach was used to solve a series of electrostatics equations. On the sides of the 3D block, it was assumed the material to be stress-free while displacement boundary conditions were imposed in the x- and y-directions on the top surface of the PAm hydrogel. Normal deformations were disregard as the results indicated negligible normal displacements. To obtain the input for the boundary condition at the top surface of the gel, the displacement of the hydrogel was quantified by tracking the fluorescent particles embedded within the network using particle image velocimetry (PIV). The FE mesh was constructed to have 100 elements in the x- and y-direction and 60 elements in the z-direction. The contraction of the microtissues was reported as peak traction stress.

Using this approach, fluorescent images were obtained of the green beads embedded within PAm at a frequency of 9 frames per second in order to capture the contraction profile of the cardiomyocytes at 20× magnification. With the goal of obtaining the reference state, the embedded cells were removed from the GelMA structure afterwards using a dissolving solution comprised of ammonium hydroxide and Triton-X 100. After the removal of cells, the PAm gels embedded with beads were re-imaged to obtain the reference state. By comparing the reference state to the images captured during the contraction of the cells, the displacement field using PIV was obtained. Using the FE approach, the traction stress field caused by the cellular forces was calculated.

Laser Scanning Confocal Microscopy for Imaging Stained Cardiomyocytes:

An acellular GelMA patterned structure within the microfluidics device was made with red fluorescent beads in the GelMA hydrogel and green fluorescent beads embedded within the polyacrylamide gels. An Olympus UMPlanFl 10× water immersion objective lens mounted onto a Leica SP5 microscope was used for imaging. The scan speed was set to 400 Hz, with z-step size of 0.74 µm. The green beads were visualized using a 488 nm laser, while a 594 nm laser was to visualize the red beads. Sequential scanning was utilized to individually image the green and red fluorescent beads to minimize unwanted excitation of the channels.

Immunofluorescent Staining with Fluidics Device:

The microfluidic chip was removed from a 37° C. incubator and disconnected from the media input before being washed with PBS twice to clean out remaining media. Next, a formaldehyde solution (1:10 dilution in PBS) was introduced into the device and incubated at room temperature for 10 minutes. After washing three times with PBS at 10-minute intervals, a collagen type II solution (0.1% in PBS) was introduced into the device and incubated at room temperature for 15 minutes. After washing three times with PBS at 10-minute intervals, the device was washed with blocking buffer (3% bovine serum albumin and 0.1% Triton-X 100) and incubated at room temperature for 45 minutes. Anti-Connexin-43 rabbit antibody (Sigma-Aldrich) diluted 1:400 in blocking buffer was then introduced into the device. The device was incubated in a humidity chamber for 2 hours. After washing three times with PBS at 10-minute intervals, green secondary goat-anti-rabbit antibody (1:250 dilution in blocking buffer) was introduced into the device and incubated for 2 hours. After washing three times with PBS at 10-minute intervals, hoechst 33342 (1 µg/mL) and cell mask were introduced into the device and the inlet and outlet ports were sealed with tape prior to imaging.

Quantification of MCF7 Spheroids Growth within GelMA Hydrogel Structures:

Brightfield images of the GelMA hydrogels containing the spheroids and HUVECs were recorded as a function of culture time (1-5 days) to examine their growth post-encapsulation. The area of the spheroid was quantified by tracing the boundary of the spheroid using the free-hand selection tool on ImageJ.

Immunofluorescence Staining of HUVECs:

Cells within the device were fixed in 10% Paraformaldehyde (PFA) solution for 10 minutes at ambient temperature followed by infusing the device with PBS to remove the excess PFA. Blocking buffer, comprised of 0.1% Triton-X100 and 3% Bovine Serum Albumin (BSA), was added and the cells were incubated in this solution for 30 minutes at ambient temperature. The device was washed with PBS after each step to remove the residual solutions. The fixed cells were treated overnight with rabbit polyclonal VE-Cadherin antibody (Cat. No. D87F2, Cell Signaling) diluted in blocking buffer at 4° C. The primary antibody solution was removed by washing with PBS. The device was incubated in blocking buffer containing Alexafluor 488 goat anti-rabbit secondary antibody (Cat. No. A-11008, Thermo-Fisher Scientific) and Rhodamine-conjugated Phalloidin (Cat. No. R415, ThermoFisher Scientific) for 70 minutes at room temperature. The cells were subsequently washed with PBS and stained with 20 µg/mL DAPI solution for 20 minutes to visualize the nuclei. The device was rinsed several times with PBS and imaged using a confocal microscope.

Doxorubicin Solution:

Doxorubicin (Cat. No. D1515, Sigma-Aldrich) was weighed and dissolved in DMSO to achieve a concentration of 100 mg/mL. This solution was distributed into small aliquots and stored in −20° C. The stock solution was thawed and diluted to 100 µg/mL in pre-warmed MM (~37° C.) and sterilized using a DMSO-resistant syringe filter (Pall Corporations). This 100 µg/mL solution was further diluted in MM to acquire doxorubicin concentrations of 1 and 10 µg/mL used herein.

Penetration of Doxorubicin into Spheroid-Laden GelMA Structures:

The cell-laden GelMA hydrogels were exposed to MM containing 1, 10, and 100 µg/mL Doxorubicin. The presence of Doxorubicin within the spheroids was detected using a Zeiss Observer A1 Microscope with a 10× A-Plan lens after 3 days of incubation on the red fluorescent channel. An exposure time of 700 ms was used for all samples.

Confocal Microscopy for Imaging Immunofluorescent Stained Cells:

Laser scanning confocal microscope was used to obtain Z-stack images of cells stained for nuclei, F-Actin, and VE-Cadherin as well as for the PAm hydrogels embedded with fluorescent beads. A vertical step size of 1 µm was used to acquire the Z-stack images.

Effect of Flow Rates on Mechanical Compression of the GelMA Hydrogels:

To determine whether the GelMA structures are differentially compressed at different flow rates, acellular structures containing 2% (v/v) fluorescent beads of 200 nm diameter (Cat. No. F8782, ThermoFisher Scientific) were used. The fluorescent bead laden-GelMA hydrogels were perfused with MM and allowed to equilibrate for 6 hours at 37° C. The equilibrated structures were subjected to different flow rates of 10, 20, 40, and 1000 µL/h. The X-Y images of the hydrogels subjected to different flow rates at 37° C. were acquired by using a spinning disk confocal microscope. The reference state was generated by recording the X-Y section of the ellipse hydrogel structure at a z-position that bisects the top and bottom of the chamber in the absence of any flow. The samples were then exposed to different flow rates and the X-Y images were recorded at the same z-position that was used for the reference state. The 2-D displacement fields, u and v, were obtained by comparing the reference image to the images recorded under different flow rates using Particle Image Velocimetry (PIV). The area strain, $A_{strain}$, was calculated by using the following equation:

$$A_{strain} = \frac{\partial u}{\partial x} + \frac{\partial v}{\partial y} \quad \text{(Eq. 7)}$$

Modeling of Mass Transfer within the Cell-Laden GelMA Hydrogel Structures.

COMSOL Version 4.2 was used to solve the 2-D diffusion-reaction equation (Eq. 1, 6) with a convective boundary condition (Eq. 3). The domain of the system was comprised of an ellipse structure with major and minor axes lengths of 1.2 and 0.45 mm, respectively.

Figure 4:
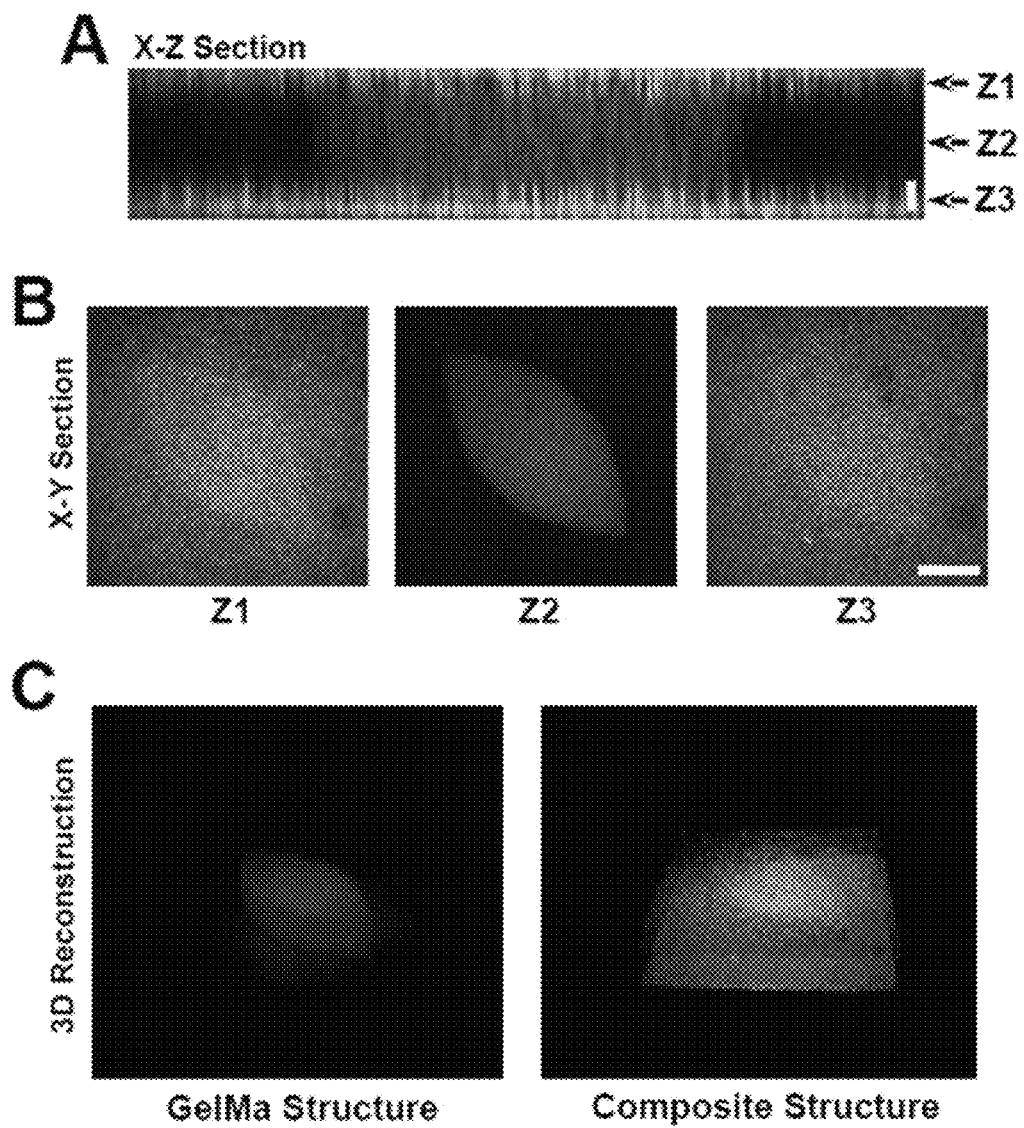
FIG. 4A-C presents the characterization of patterned hydrogel structures within a flow chamber. Z-stack images of the hydrogels were obtained using a laser scanning confocal microscope. The X-Z cross-section (A) and the corresponding X-Y planes at different Z locations (B) are shown. GelMa and the PAm hydrogels were embedded with red and green fluorescent particles, respectively, to visualize the structures. Horizontal scale bar: 100 µm. Vertical scale bars: 10 µm. (C) 3D rendering of the GelMa hydrogel (Left Panel) and the composite structure showing both the PAm and GelMa hydrogels (Right Panel) are shown.

Characterization of GelMA Structures within Microfluidic Device:

Red fluorescent particles (200 nm) were incorporated in an acellular GelMA solution prior to polymerization to visualize the structures within the device. By using a spinning disk confocal microscope, z-stack images of the GelMA structures were obtained along with PAm hydrogels. The X-Z sections illustrate that the GelMA structures comprising the red particles have an approximate thickness of 120 μm, which is encased above and below by PAm hydrogels comprising green particles having an approximate thickness of 70 μm (see FIG. 4A). The X-Y sections at the indicated Z positions demonstrate that the PAm hydrogels have a planar structure while the GelMa gels have an ellipsoid structure (see FIG. 4B). A 3D rendering of these structures is shown in FIG. 4C with the left and right panels indicating the GelMA, and the GelMA with PAm structures, respectively.

Figure 6:
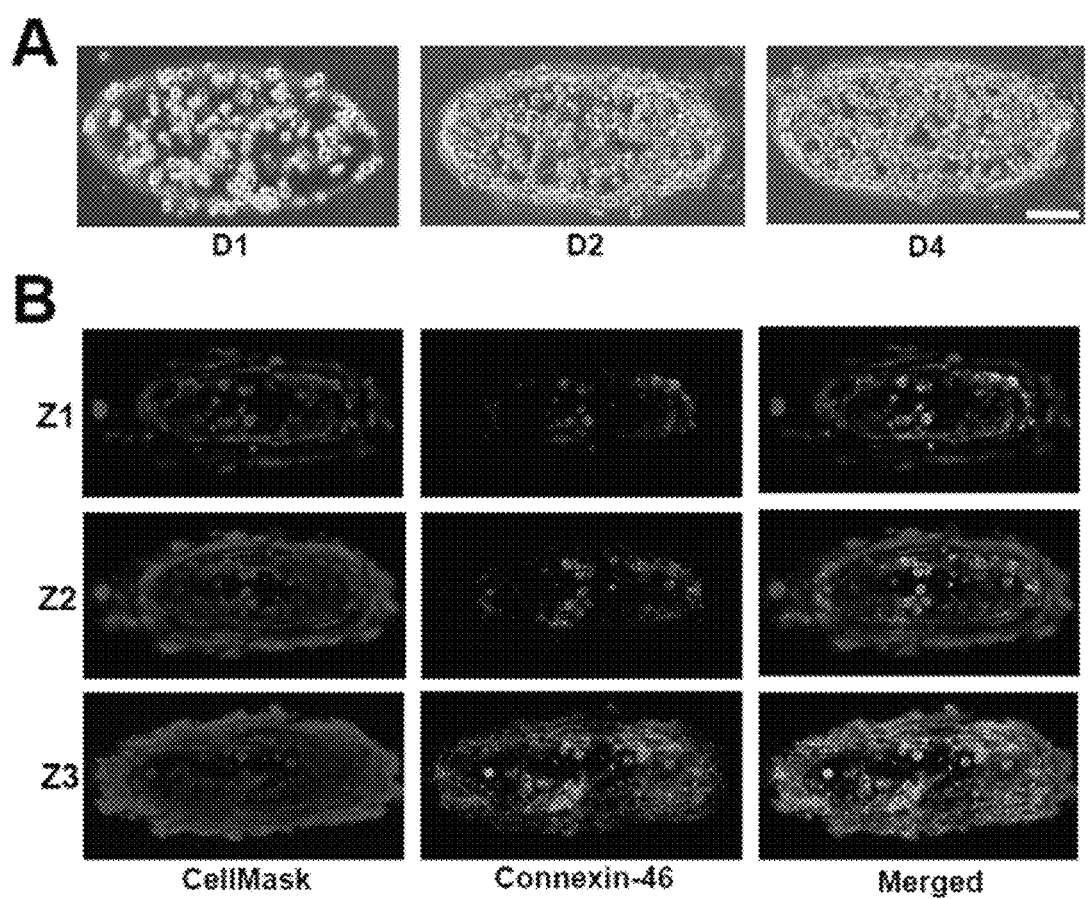
FIG. 6A-B presents the organization of encapsulated cells within patterned GelMa structures. (A) Cell density within the GelMa structures increased as a function of culture time. (B) X-Y confocal sections of cells ubiquitously stained with CellMask and immunostained for Connexin-46. The presence of fibroblasts amongst the encapsulated cells is suggested by connexin-46 negative staining. The Confocal sections proceed from the top, Z1, to the bottom, Z3, of the patterned GelMa structures. Scale bar: 100 µm.

Cellular Organization within Cardiac Microtissues:

To assess whether our platform can maintain and support cardiomyocyte function, neonatal mouse cardiomyocytes were encapsulated within GelMA structures in the fluidics device. The fluidics device was subsequently infused with cardiomyocyte maintenance media. The changes to the cells within the microtissues were monitored. Differential interference contrast (DIC) images of the GelMA structures indicated an increase in cell number as a function of culture time (see FIG. 6A). Due to the inability of the cardiomyocytes to proliferate, any observed growth was attributed to the inclusion of fibroblasts during the cardiomyocyte isolation process. The cellular composition of the microtissues was characterized after 7 days of culture by ubiquitously visualizing the cells using CellMask and identifying the cardiomyocytes by staining for Connexin-43. Confocal sections of the stained cells indicated that the cells which were positive for Connexin-43 were located within the interior of the microtissues (see FIG. 6B). The number of connexin-positive cells increased at confocal sections approaching the bottom of the microtissues, Z1 to Z3 (see FIG. 6B). A substantial population of cells was found to be positive for Connexin-43 within these structures.

Figure 7:
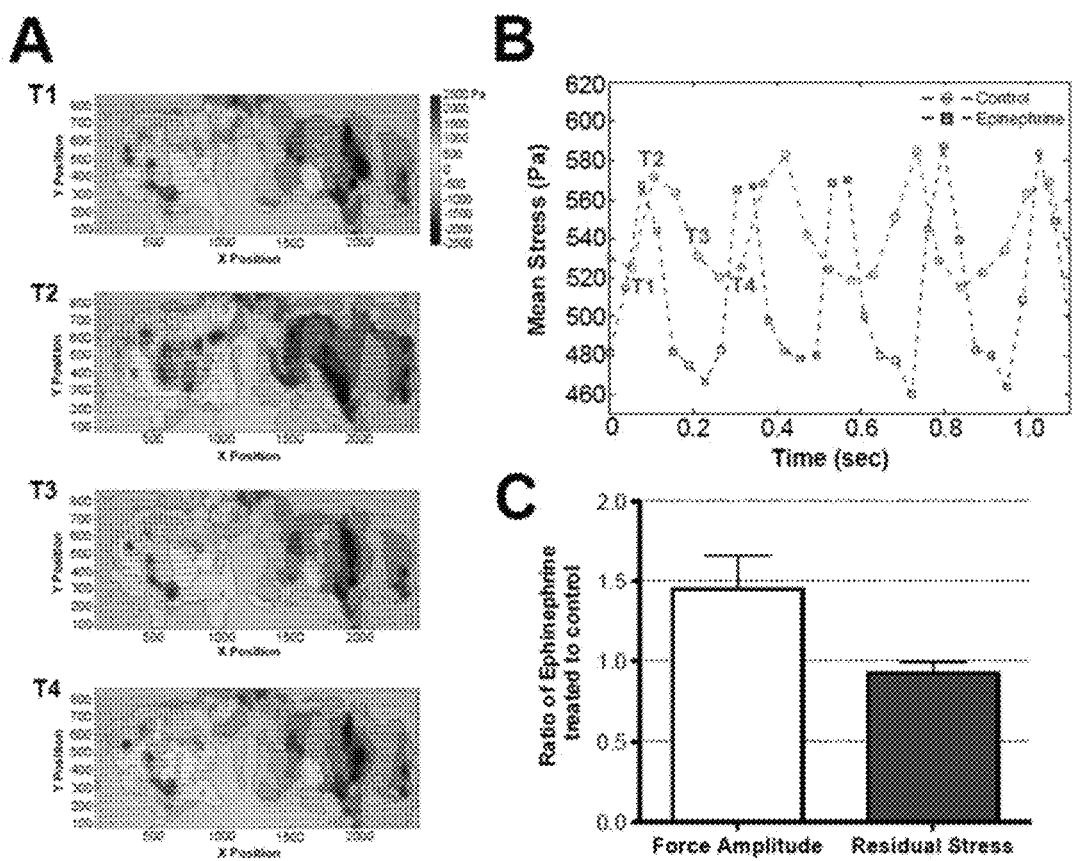
FIG. 7A-C provides for the quantification of contractile forces within patterned GelMa structures. (A) The planar displacements, shown as a vector field, and the traction stresses along the major axis of the patterned GelMa structures, shown as a heat map, were measured from the PAm hydrogels. The times associated with each graph, T1 through T4, are shown in (B). The X- and Y-axis of the graphs indicate the physical location of the measured quantities while the values within the heat map are indicated by the color bar. (B) A representative plot of the mean traction stress as function of time in absence (red circles) and presence (blue circles) of epinephrine. The stresses along the major axis of the patterned GelMa structures were used for calculating the mean value (C) The ratio of force amplitude and residual stress in the presence of epinephrine to absence of epinephrine measured from multiple µtissues. Values lower than or higher than 1 indicates a decrease or increase in force amplitude and residual stress, respectively, while a value of 1 suggests the lack of change.

Real-Time Contractile Force Measurements:

Cardiomyocytes entrapped within the GelMa structures were cultured for 7 days within the microfluidics device prior to assessing their contractile forces. The deformation of the PAm gels was obtained by comparing the location of the embedded fluorescent particles during the contraction and after the removal of cells from the device. The left panel in FIG. 7A illustrates the displacement of the particles during the contraction-relaxation cycle of the cardiomyocytes. Interestingly, the non-zero displacement field during the relaxation phase of the contraction cycle indicates that the cardiomyocytes apply residual traction stresses onto the GelMa structure even without actively contracting. Using this displacement field and finite element analysis, the contractile stresses were quantified during the contraction cycle (right panel in FIG. 7A). The traction forces exhibit stresses that are higher along the major axis of the ellipse compared the stresses along the minor axis. By using only the mean traction stress value in the direction of the major axis of the ellipse, a time-force plot was generated that shows oscillatory changes in the contraction of the cardiomyocytes indicative of the contraction-relaxation cycle of a beating heart tissue (see FIG. 7B).

Furthermore, the effect of epinephrine on the contraction profile of the microtissue was assessed. To this end, the changes in the time-force plot for the same GelMa structure in the absence and presence of epinephrine was quantified. FIG. 7B illustrates that when the cells are exposed to the drug the frequency and amplitude of a contraction-relaxation time profile was increased. Interestingly, slight decreases in the residual stresses in the relaxed state of the contraction cycle were observed. By plotting the ratio of the force amplitude and residual stress in the presence or absence of epinephrine, the drug's effect on multiple microtissues was examined (see FIG. 7C). The results illustrate a measured force amplitude ratio of ~1.4 and residual stress ratio of ~0.9. Values greater than one indicate a measured increase. Values lower than one indicates a measured decrease. The results suggest that epinephrine increases force amplitude while decreasing residual stress in comparison to the control.

Quantification of Cell Motility within the Cell-Laden GelMA Hydrogel Structures.

Figure 9:
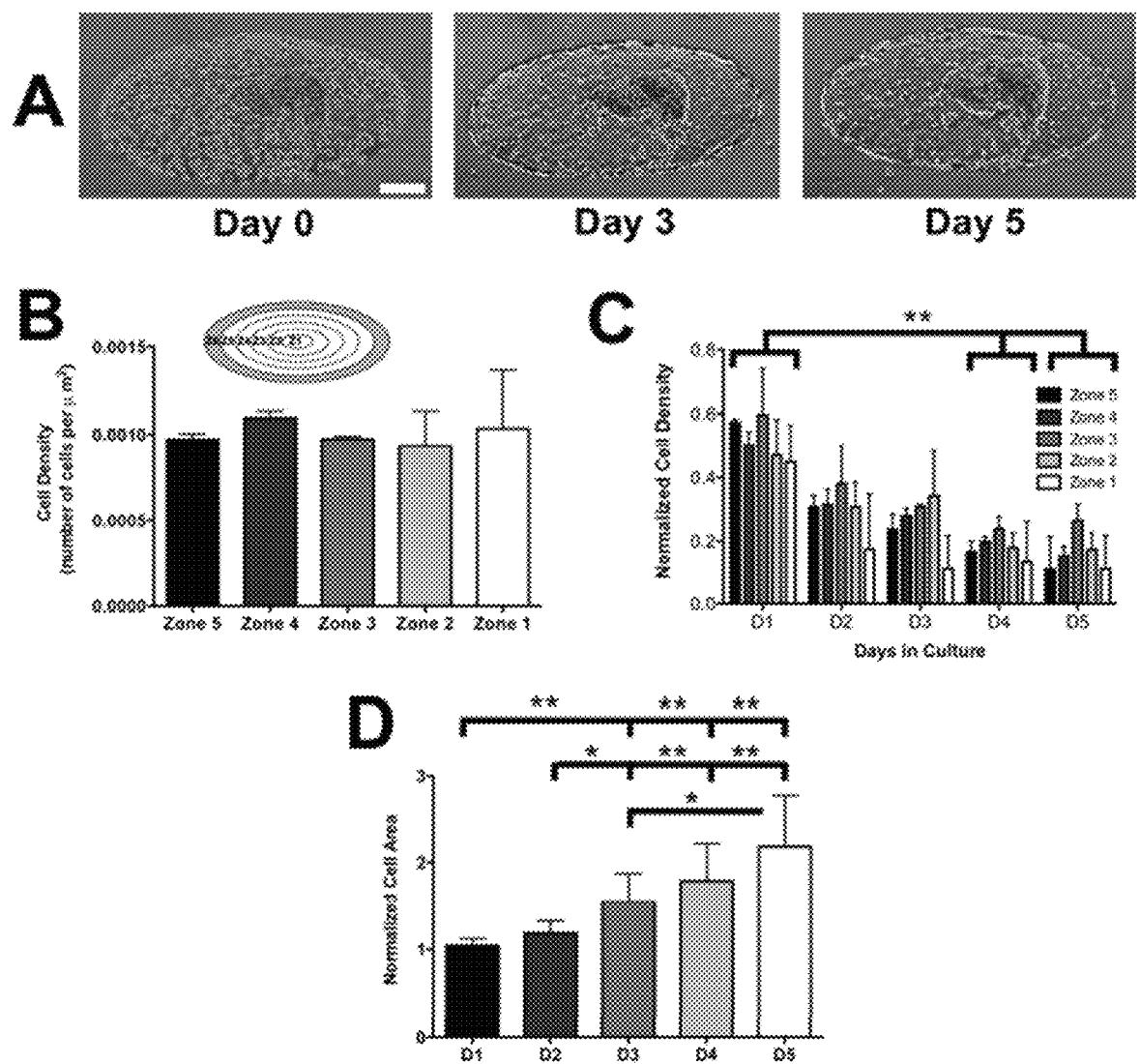
FIG. 9A-D shows co-culture of HUVECs and MCF7 spheroids within GelMA structures. (A) Bright field images of HUVECs co-cultured with MCF7 spheroids at immediately after encapsulation (D0), Day 3 (D3), and Day 5 (D5). Scale bar: 200 μm. (B) Cell density within Zones 1 through 5 on D0 within the GelMA hydrogel. Different zones are indicated within the inset. The shaded peripheral region in the diagram, Zone 6, is excluded from the quantification. (C) Changes in the normalized zonal density of HUVECs with culture time. Within each zone, the cell density monitored as a function of culture time was normalized to D0 density and was plotted in the bar graph. (D) Spheroid size, quantified by 2-D area and normalized to D0 size, as a function of culture time. and ** indicate statistically significant differences of p<0.05 and 0.01, respectively, as obtained from pair wise t-test. In (C), differences were reported only if the changes in normalized cell density were statistically significant in all zones (Zone 1-5) between different culture days.

The motility of HUVEC cells and MCF7 spheroids was determined by examining the changes in their local cell density within the GelMA hydrogel as a function of culture time. Brightfield images of the cell-laden GelMA hydrogels were taken for up to 5 days. A custom Matlab software was used to process the bright field images of the cell-laden GelMA hydrogel by identifying the boundary of the hydrogel structure and partitioning it into smaller zones of Z1 to Z6 as indicated in FIG. 9B inset. In order to partition the structure into smaller zones, a Sobel filter was applied to the bright field image of the cell-laden GelMA hydrogel to identify its boundaries. High-pass filter was applied to remove random non-zero values outside the GelMA hydrogel structure. A distance transform was applied to the filtered image resulting in small and large values within the interior and exterior of the ellipse GelMA hydrogel, respectively. The ellipse structure of the cell-laden GelMA hydrogel was identified by applying a low-pass filter onto the distance transform image and converting the filtered results into a binary image. Finally, a built-in Matlab function, Region-props, was used to identify the centroid, major, and minor axes lengths of the ellipse hydrogel structures. Smaller ellipses were created by reducing the major and minor axes of the outer ellipse structure to create multiple zones as in FIG. 9C.

The local cell density was obtained by counting the number of cells divided by the area of each zone. Zone 6 was excluded from all analysis since the number of cells at the perimeter of the ellipse cannot be accurately counted. For quantifying the flow-rate dependent migration of cells in FIG. 10B, zones 1 through 5 were merged to form a single area.

Formation and Characterization of Trilayer Hydrogel-Based Device.

Figure 11:
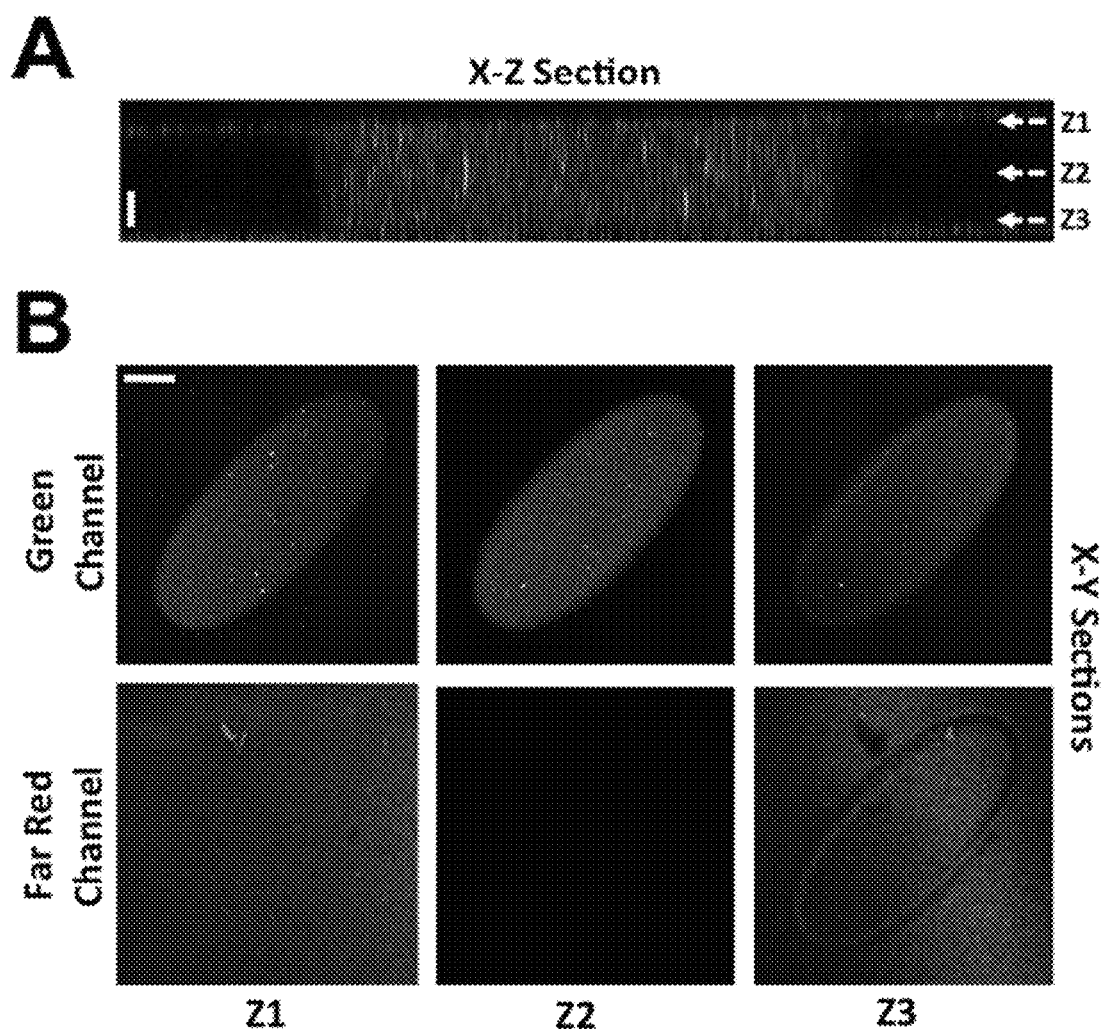
FIG. 11A-B shows characterization of the device. (A) X-Z confocal sections of a photo-patterned GelMA hydrogel sandwiched between two PAm hydrogels. Far red and green fluorescent beads are used to visualize the PAm and GelMA hydrogels, respectively. Scale bar: 50 μm. (B) X-Y confocal sections of the green and far-red channels at Z positions— Z1, Z2, and Z3—listed in (A). Scale bar: 200 μm.

GelMA hydrogels were photopatterned within a microfluidics device to achieve an ellipse structure with major and minor axes lengths of 1.2 mm and 0.45 mm, respectively. A X-Z confocal section of the fluidic chamber depicts a structure embedded with green fluorescent particles sandwiched between two PAm hydrogels containing far red particles (FIG. 11A). The non-adhesive PAm hydrogels were used to eliminate the adhesion (if any) of the encapsulated cells to the surfaces outside GelMA structures. The X-Y confocal sections showed the presence of a tri-layer hydrogel as sections at Z1 and Z3 show both the GelMA and PAm hydrogels while Z2 only shows the GelMA hydrogel (FIG. 11B). The time-lapse recording of the perfused device (visualized by addition of 0.1% green fluorescent beads) shows the robustness of the PAm-GelMA interface, which do not dislodge from shear forces caused by flow rates up to 80 μL/hr. Furthermore, visualization of the flow field around various portions of the GelMA structure illustrates the convective mass transport reminiscent of blood flow in vivo.

Flow Induces Concentration Gradient within GelMA Structures.

Figure 12:
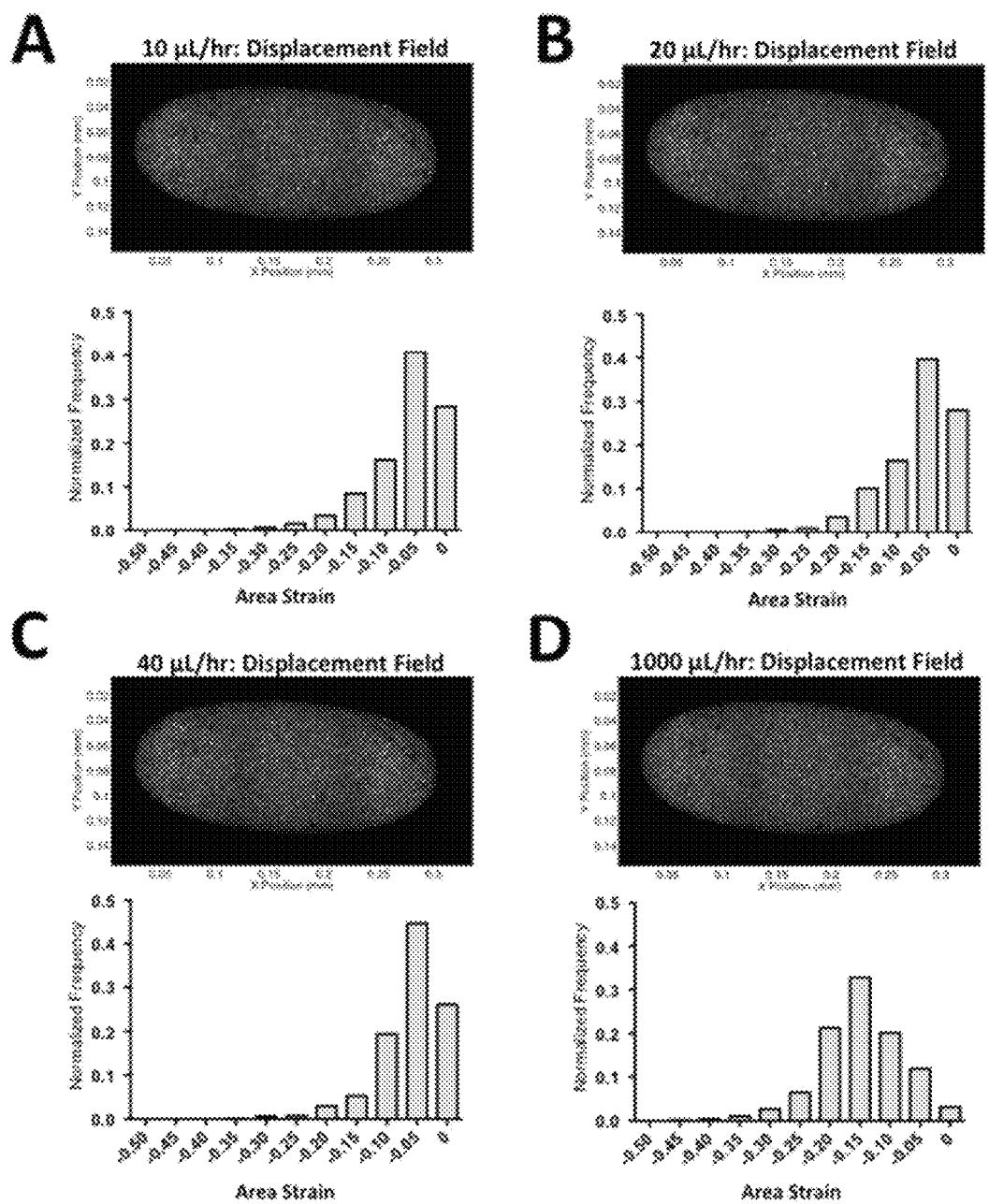
FIG. 12A-D shows flow induced compression of GelMA hydrogels. (A-D) The deformation of the GelMA hydrogel at different flow rates of 10, 20, 40, and 1000 μL/hr. The deformation of the hydrogel is depicted by (i) 2D displacement vectors overlaid onto the fluorescent images and (ii) distribution of area strain, shown as a histogram, to assess the extent of mechanical compression.

Fluid flow within the device containing cell-laden hydrogels can impart two effects—(i) compression of the GelMA structures due to increased fluid pressure and (ii) steady state concentration gradient of chemoattractants within the GelMA structures (due to their consumption by the entrapped cells). Quantification of flow rate induced changes of the GelMA hydrogels exposed to various flow rates showed no differences in their area strain up to a flow rate of 40 μL/h (FIG. 12). However, a significant change in the area strain was observed at 1000 μL/h, which was used as a positive control (FIG. 12). Area strain instead of volumetric strain was used to assess the flow induced mechanical compression because the GelMA hydrogels were confined within the fluidics channel that does not allow any vertical displacements.

Figure 13:
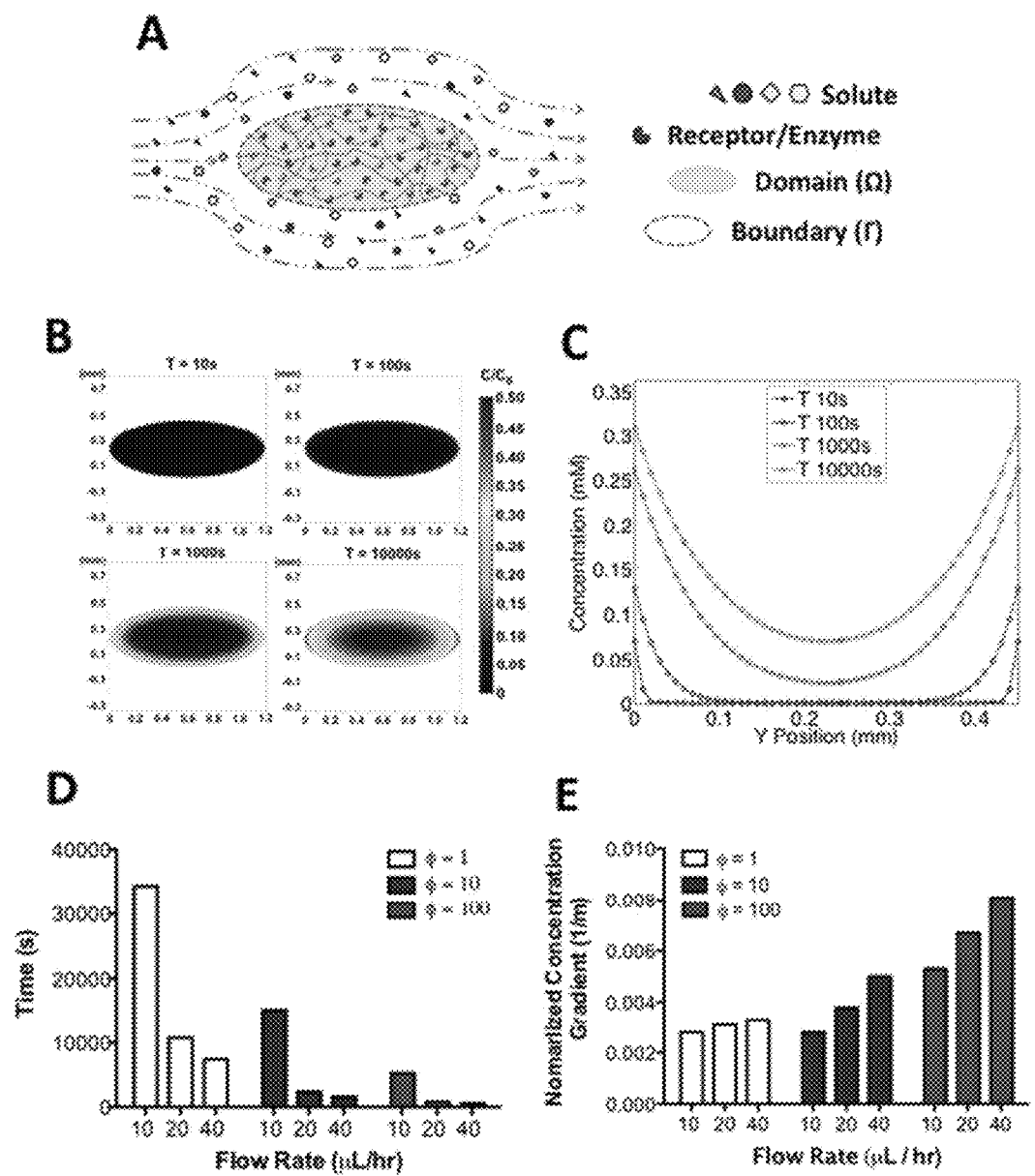
FIG. 13A-E shows concentration gradient within GelMA hydrogels. (A) Illustration of the diffusion-reaction mass transfer system with convective boundary condition. The interior of the ellipse contains encapsulated cells that consume the soluble factors supplied across the boundary of the ellipse via convection. (B) Heat map of the changes in the normalized concentration (concentration within the GelMA normalized to the bulk concentration in the media) with time. (C) Changes in the normalized concentration profile with time along the minor axis of the ellipse. Time required to reach steady state (D) and maximum normalized concentration gradient at steady state (E) for different flow rates at $\phi$=1, 10, 100.

Next the presence of a chemotactic gradient within the GelMA hydrogel exposed to different flow rates (10, 20, and 40 μL/h) was assessed. To model the concentration gradient, the convective mass transfer of an arbitrary solute from the medium (C) capable of binding to its target enzyme/receptor through a Michaelis-Menten based consumption reaction (RC) was simulated (FIG. 13A, Eq. 1).

$$\frac{\partial c}{\partial t} = D_c(\Delta \cdot \Delta C) + R_C \quad \text{(EQ. 1)}$$

Here, $D_c$ is the diffusion coefficient of solute within the GelMA hydrogel. As indicated in FIG. 13A, the domain, Ω, of the system is a 2-dimensional ellipse where the consumption of solute occurs via Michaelis-Menten kinetics (Eq. 2) while the perimeter, Γ, of the GelMA hydrogel is governed by convective flux boundary condition (Eq. 3) where the Mass Transfer Coefficient (H) is approximated from the laminar flow over a plate (Eq. 4).

$$R_C = \frac{k_{cat}E_0 C}{K_M + C} \quad \text{(Eq. 2)}$$

$$\eta \cdot J_C = H(C(x) - C_{bulk}), \text{ for } x \in \Gamma \quad \text{(Eq. 3)}$$

-continued $$H = \frac{2 D_C Sc^{1/3} Re^{1/2}}{3L} \quad \text{(Eq. 4)}$$

$$Sc = \frac{\mu}{\rho D_C}, \quad Re = \frac{\rho v l}{\mu} \quad \text{(Eq. 5)}$$

In the above equations, $k_{cat}$ is the catalytic coefficient, $E_0$ is the enzyme concentration, $K_M$ is the Michaelis constant, L is the characteristic length, and $C_{Bulk}$ is the concentration of solute in the bulk solution. Furthermore, the Michaelis-Menten reaction was linearized by assuming that the substrate concentration is much less than $K_M$ since high cell density within the hydrogels would increase the consumption rate of solutes such that their concentration remains substantially low. With this assumption, Equation 2 can be simplified as follows:

$$R_C = (k_{cat}/K_M)E_0 C \quad \text{(Eq. 6)}$$

Based on this theoretical framework, the mass transfer was modeled of an arbitrary solute of molecular weight (MW) 75 kDa, more common for serum proteins, whose $D_C$ within the GelMA hydrogel was approximated to be 10 μm²/s. The concentration and the catalytic efficiency of the enzyme consuming this soluble factor was designated to be 100 nM and 10 mM⁻¹min⁻¹, respectively, based on common enzymes found within the cytosol. In addition, the resulting concentration profile as a function of time is shown as 2-D heat maps and concentration profiles along the minor axis in FIGS. 13B and 13C, respectively. These plots suggest that the concentration of solute was substantially higher at the periphery than at the center of the GelMA structure at all time points. This is mainly due to the consumption of the solute by the encapsulated cells. Therefore, at steady state (at 10000 s), a large concentration gradient was established within the GelMA structure indicating the presence of a chemotactic gradient (FIG. 13C).

Figure 14:
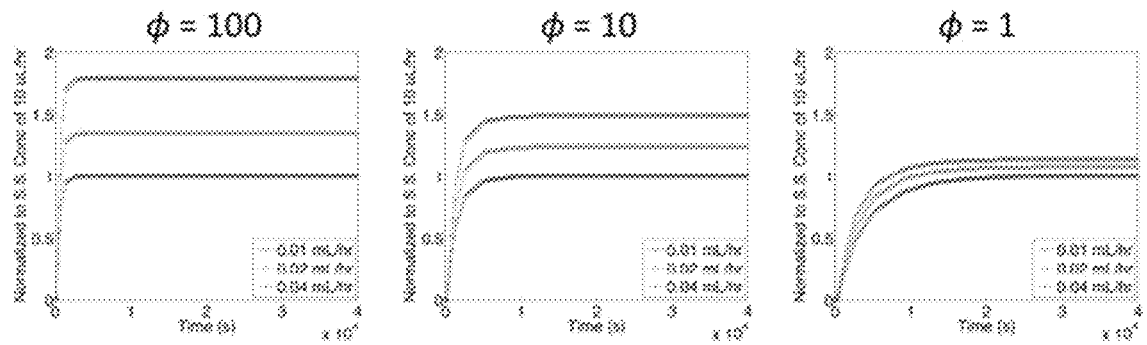
FIG. 14 shows transient concentration changes within the GelMA hydrogel. The normalized concentration, defined as the ratio of the concentration within the hydrogel to the bulk concentration, at the center of the ellipse as function of time for different flow rates and e values. Here, e is a non-dimensionalized parameter that compares the diffusion to the consumption of a solute.

To generalize the model to any protein or biomolecule, it was further examined how the concentration profile changes as a of ϕ, which is defined as a ratio of $D_C/A_E$ to $(k_{cat}/K_M)E_0$, where $A_E$ is the perimeter of the ellipse multiplied by the height of the fluidics chamber. Here, ϕ is a non-dimensionalized parameter that compares the diffusion of a solute to its consumption rate. The results indicate that increasing flow rates (X-Y) reduces the time required to reach steady state concentration profile at all ϕ values (FIG. 13D and FIG. 14).

Figure 15:
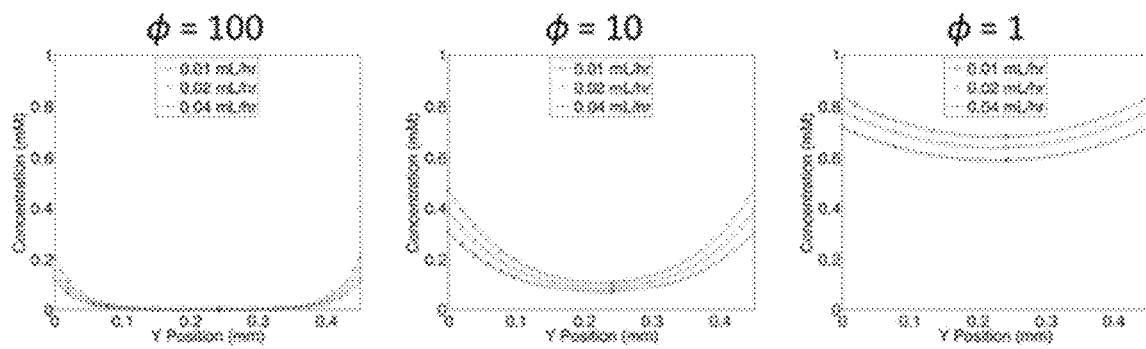
FIG. 15 shows the steady state profile within the GelMA hydrogel. The normalized concentration (the ratio of the concentration within the hydrogel to the bulk concentration) profile along the minor axis of the ellipse structure for different flow rates and e values.

The examination of steady state concentration profile indicates increase in concentration gradient throughout the entire ellipse structure with increase in flow rates (FIG. 13E and FIG. 15). On the other hand, the concentration gradient decreases in the ellipse structure with decreasing ϕ value. The results indicate that the increase in flow rate exposes the cells within the GelMA hydrogels to greater concentration gradients even at an early time point after encapsulation.

Migration of HUVECs to the Periphery of 3D GelMA Structures.

Figure 10:
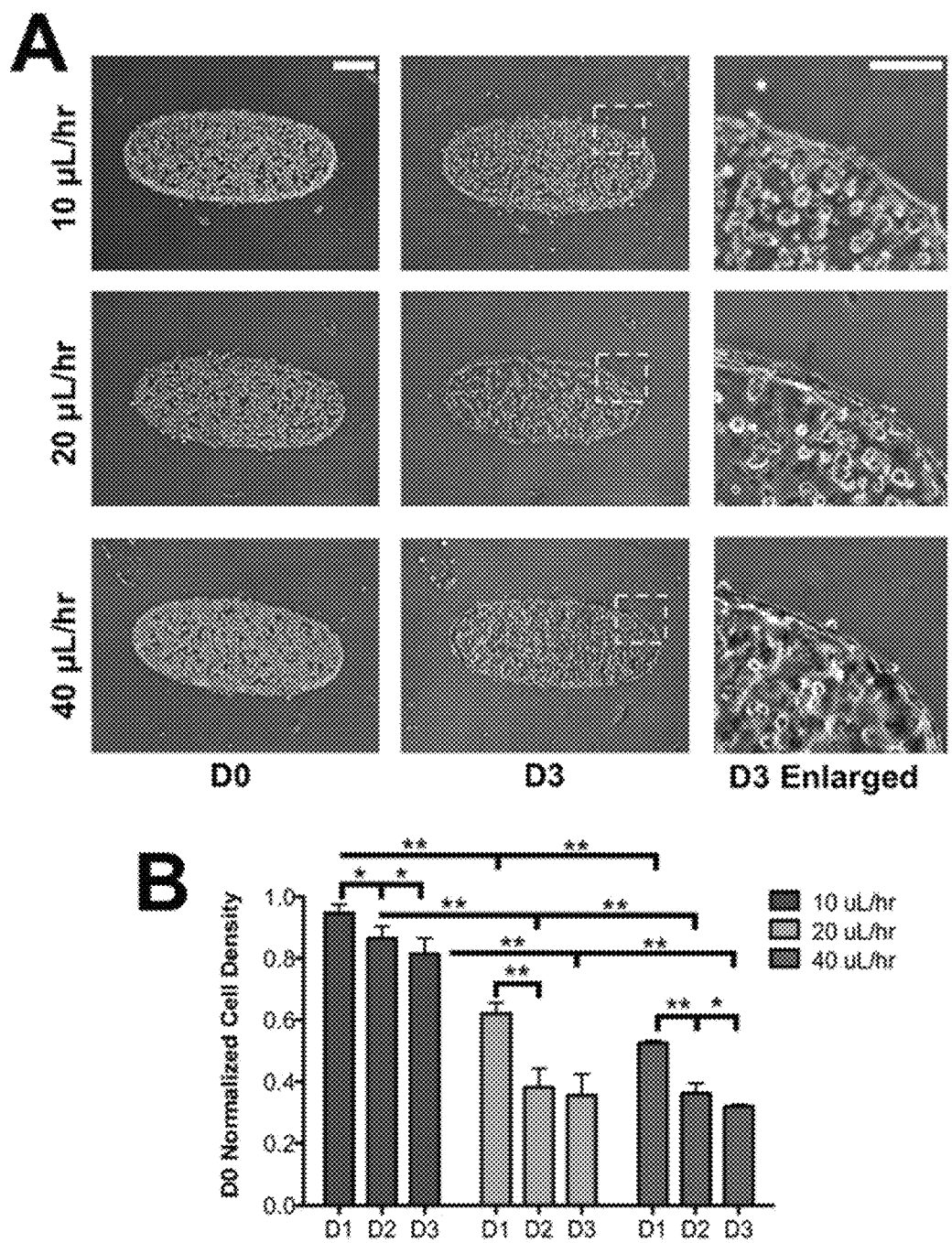
FIG. 10A-B shows flow-induced migration of encapsulated HUVECs. (A) Bright field images of HUVECs within GelMA hydrogels as a function of culture time. Each row represents different flow rates while the 1st and 2nd column represent different culture days –day 0 (D0) indicates the day of encapsulation. Scale bar: 200 μm. The 3rd column represents a magnified image of the region identified by a square window with yellow dashed lines in each row of day 3 (D3) images. The red arrows indicate the HUVECs at the periphery of GelMA structure. Scale bar: 30 μm. (B) The change in local density of HUVECs at different culture times for flow rates of 10, 20, and 40 μL/hr. The y-axis represents the local cell density quantified at specified culture day normalized to D0 cell density. * and ** indicate statistically significant differences of p<0.05 and 0.01, respectively, as obtained from pair wise t-test.
Figure 19:
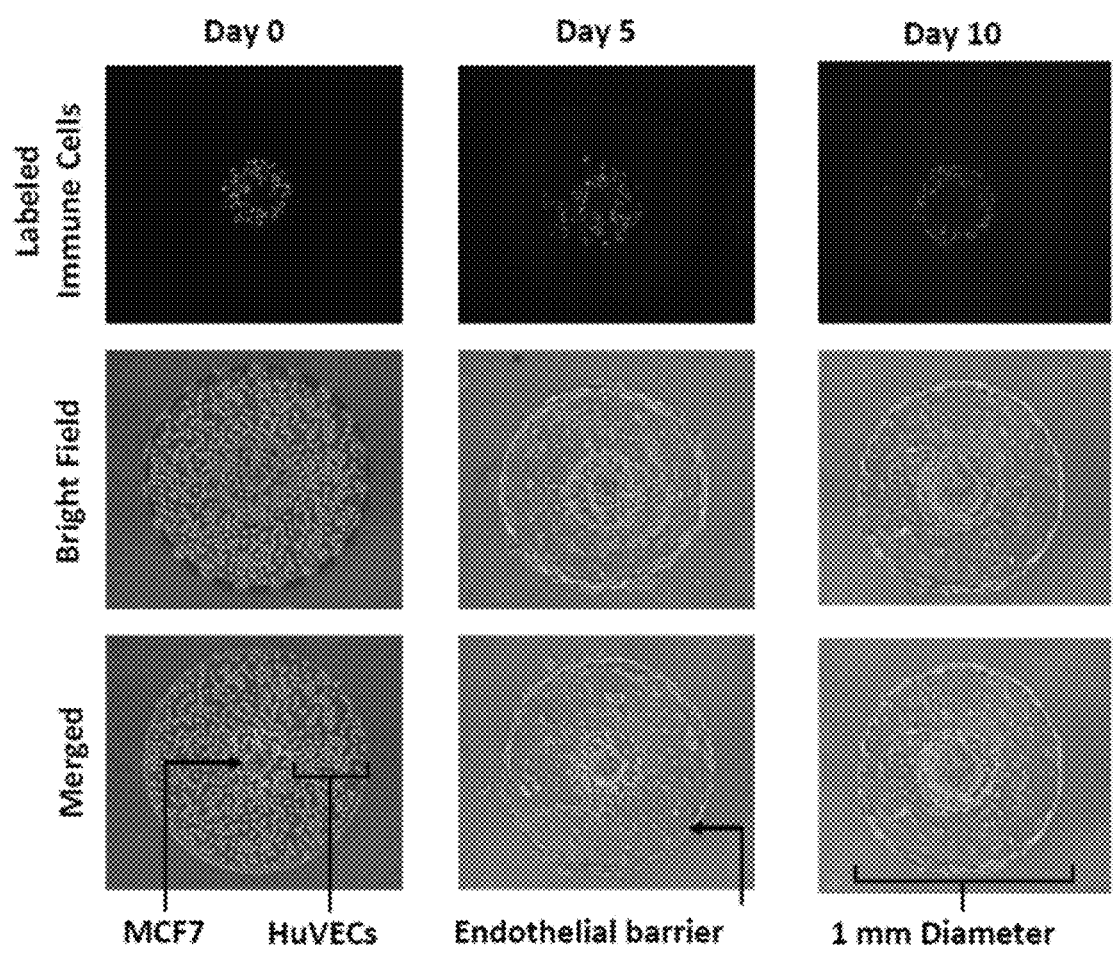
FIG. 19 shows Tri-culture system created from an additive photopatterning approach within a microfluidics device. The tri-culture system is comprised of cancer cell spheroid (MCF7), endothelial cells (HuVECs), and immune cells (labeled green cells). The additive approach was used as follows: (i) a hydrogel precursor solution containing cancer spheroid and immune cells were introduced into the device and an inner hydrogel cylinder (shown in red circle, left column) formed using photopolymerization (ii) the surrounding unpolymerized solution along with the cells were washed out from the device (iii) a secondary hydrogel precursor solution containing endothelial cells were introduced and polymerized to form the larger cylinder (shown in blue circle, left column). The changes in the morphology of the tissue can be observed with time as the endothelial cells migrated to the periphery while the immune cells were retained within the interior cylinder. In addition, a qualitative increase in the size of the cancer spheroid can be observed suggesting its growth.

The above-discussed theoretical analysis predicts the existence of a chemotactic gradient that could drive the migration of HUVECs encapsulated within the GelMA hydrogels. The cell-laden structures were subjected to varying flow rates (10, 20, and 40 μL/h) for three days post-encapsulation. Brightfield images at 3 days post-encapsulation show that the cell density at the interior of the GelMA structures decreases irrespective of the flow rates with large decrease in cell density with higher flow rates (FIG. 10A Left and Center Panel) (see also FIGS. 19 and 20). The quantitative analysis of cell density across the GelMA hydrogel as a function of culture time for different flow rates supports the above observation (FIG. 10B). It was also observed differences in the spatial distribution of cells within the GelMA hydrogel under different flow rates. At 10 µL/h, the cells within the GelMA structures were uniformly distributed at day 3 (FIG. 10A Center Panel). On the other hand, flow rates of 20 and 40 µL/h resulted in the migration of most of the HUVECs to the periphery of the GelMA hydrogel structure (FIG. 10A Left and Center Panel, 10B). The thickness of the HUVEC layer at the periphery of the GelMA hydrogel was found to be decreased for 40 compared to 20 µL/h flow rate (FIG. 10B right panel). For the remainder of the studies, cultures exposed to a flow rate of 40 µL/h were used.

Co-Culture of HUVECs and Cancer Cell Spheroids.

It was examined whether the migration of encapsulated HUVECs to the periphery of the GelMA hydrogel will persist in the presence of cancer spheroids. Brightfield images of the encapsulated cells at days 0, 3, and 5 reveal that the HUVECs indeed migrate to the periphery of the GelMA structures even in the presence of MCF7 spheroids (FIG. 9A).

The migration of HUVECs at smaller time increments was investigated by quantifying the changes in the local cell density as a function of time. To this end, the ellipse structure was partitioned into different zones, and quantified the cell density in each zone as a function of culture time. Immediately after encapsulation, the density of the encapsulated HUVECs across Z1 to Z5 was found to be uniform, suggesting a homogenous distribution of cells within the GelMA hydrogel structures (FIG. 9B). During days 1 to 3, a large number of HUVECs migrated to the periphery of the hydrogel with a decrease of 30-40% in cell density was observed within the GelMA hydrogel. This initial migration of HUVECs to the periphery substantially declined from day 4 and onwards (only 7-10% cell density decrease was observed from day 4 onwards) (FIG. 9C).

Figure 16:
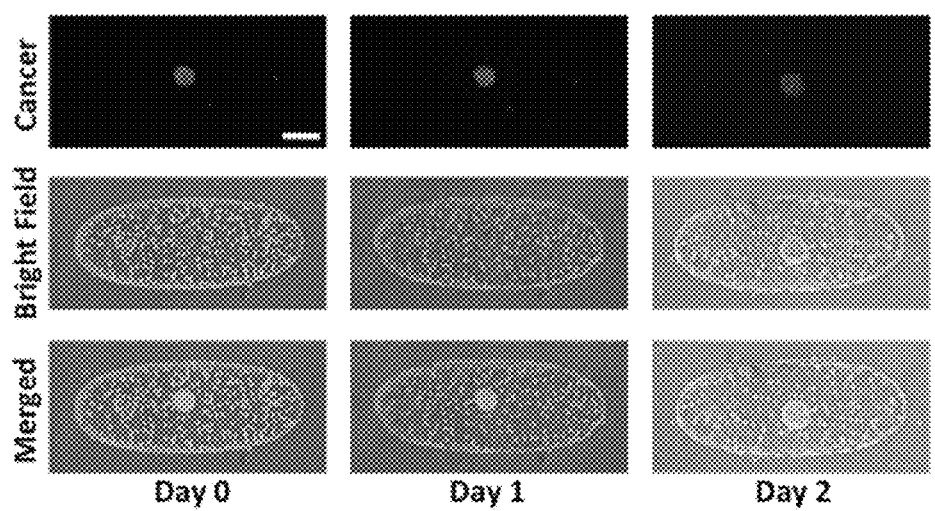
FIG. 16 shows that cancer spheroids remain clustered within the GelMA hydrogel with culture time. Brightfield and fluorescent images of HUVECs and cancer spheroid (labeled with green dye) within GelMA structures at immediately after encapsulation and after 1, 2, and 3 days in culture. Scale bar: 200 μm.

On the contrary, encapsulated MCF7 cell clusters remained intact and we did not observe migration of the spheroids or any individual cells migrating away from the spheroid. This observation was validated using labeled MCF7 cells (FIG. 16). The encapsulated cancer spheroids exhibited a gradual growth as a function of culture time (FIG. 9D). The spheroids were found to grow to approximately twice its size between days 0 and 5.

Characterization of the HUVEC Layer at the Periphery of the Hydrogel Structure.

Next was investigated whether the assembly of HUVECs around the GelMA structure forms an endothelial barrier. The cell-laden GelMA structures grown for 5 days were used to characterize the HUVEC structure. Confocal images of F-Actin and DAPI stained structures revealed the presence of HUVECs along the entire periphery (observed along the lateral and vertical directions) of the GelMA hydrogel (FIG. 17A). The HUVECs were also observed at both the GelMA-PAm interface (FIG. 17A). Interestingly, the HUVECs were found to be of single cell thickness as illustrated by the nuclei staining of the HUVECs around the ellipse (FIG. 17A, DAPI column). In addition, the presence of continuous F-actin indicates that the HUVECs form a continuous monolayer sheet along the periphery (FIG. 17A, Phalloidin column). Furthermore, to determine if cell-cell junctions are present within the monolayer sheet, the cell-laden GelMA structures were stained for VE-cadherin. Confocal images of the structures showed the presence of VE-cadherin that connects the neighboring HUVECs to form a single layer along the GelMA structure (FIG. 17B).

Dose Dependent Response of Cells within the GelMA Hydrogel to Doxorubicin.

The potential of the device as a drug screening platform was assessed by analyzing the effects of Doxorubicin on HUVEC barrier and the tumor spheroids. Cell laden GelMA structures, cultured for 5 days, were exposed to different concentrations of Doxorubicin (1, 10, and 100 µg/mL) for 3 days. The penetration of Doxorubicin into the cancer spheroids was investigated by using fluorescent imaging. The results indicate an increased accumulation of Doxorubicin in samples treated with 10 and 100 µg/mL of drugs (FIG. 18A). However, minimal accumulation of Doxorubicin was observed in samples treated with 1 µg/mL concentration (FIG. 18A). Brightfield images of cancer spheroids before and after 3 days of Doxorubicin exposure suggested a decrease in spheroid size and the darkening of the MCF7 spheroids exposed to 10 and 100 µg/mL Doxorubicin (FIG. 18B). To quantify the effects of Doxorubicin, the changes in spheroid size was analyzed before and after treatment with varying concentrations of the drug. MCF7 spheroids exposed to 10 and 100 µg/mL Doxorubicin experienced ~7 and ~15% decrease in spheroid area. On the other hand, the growth of the cancer spheroid was still observed at 1 µg/mL although the growth was ~20% less than those cultured in the absence of the drug (FIG. 18C). In addition to cancer spheroids, the drug was also found to be cytotoxic to HUVECs cells as the endothelial barrier was found to have disappeared upon exposure to Doxorubicin. This finding is consistent with other reports, which showed the cytotoxic effect of Doxorubicin on endothelial cells A number of embodiments have been described herein. Nevertheless, it will be understood that various modifications may be made without departing from the spirit and scope of this disclosure. Accordingly, other embodiments are within the scope of the following claims.

What is claimed is:

1. A method for in vitro cell culture and screening comprising:
   (a) providing a cellular composition comprising cells in a polymerizable media of gelatin methacrylate, ascorbic acid and a photoinitiator;
   (b) providing a microfluidic device, comprising:
      (i) an inlet channel;
      (ii) an outlet channel;
      (iii) an optically translucent or transparent cell culture chamber fluidly connected between the inlet and outlet, wherein the chamber comprises a biocompatible layer for cell binding having one or more patterned hydrogels of natural polymers which comprise photoreactive side groups;
   (c) flowing the cellular composition from the inlet to the outlet of said microfluidic device such that the cells in the cellular composition flow to, and bind to the one or more patterned hydrogels; and
   (d) polymerizing the cellular composition at the one or more patterned hydrogels of natural polymers with UV light to obtain cellular islands.

2. The method of claim 1, wherein the cellular composition comprises stromal cells and/or parenchymal cells.

3. The method of claim 2, wherein the stromal cells are fibroblasts.

4. The method of claim 2, wherein the parenchymal cells are cancer cells.

5. The method of claim 1, wherein the cell culture chamber comprises opposing surfaces coated with polyacrylamide and methacrylate.

6. The method of claim 1, further comprising contacting the cellular islands with a test agent.

7. The method of claim 1, wherein the natural polymers are selected from hyaluronic acid, gelatin, chitosan, and cellulose.

8. The method of claim 1, wherein the photoreactive side groups are cinnamate groups, acrylate-based groups, or combination thereof.

9. The method of claim 1, wherein cellular islands comprise gelatin methacrylate.

10. The method of claim 1, wherein the cellular islands comprise embedded cells.

11. The method of claim 10, wherein the cells are cancerous cells or endothelial cells.

12. The method of claim 10, wherein the cells are from the digestive system, musculoskeletal system, respiratory system, urinary system, reproductive system, endocrine system, cardiovascular system, lymphatic system, nervous system, or integumentary system.

13. The method of claim 10, wherein the cells are from the liver, heart, or skeletal muscle.

14. The method of claim 10, wherein the cells are stem or progenitor cells.

15. The method of claim 1, wherein the cells are genetically engineered.

16. The method of claim 1, wherein the cellular composition is polymerized by a photomask-based stereolithography approach coupled with the photogelation of polymers.

17. The method of claim 1, wherein the cell culture chamber further comprises a top hydrogel attached or tethered to the top of the chamber and/or wherein the cell culture chamber comprises a bottom hydrogel attached or tethered to the bottom of the chamber.

18. The method of claim 1, wherein the cell culture chamber comprises a polymer that is inert and resists re-molding by cells.

19. The method of claim 18, wherein the polymer is polyacrylamide.

20. The method of claim 1, further comprising fabricating said microfluidic device, comprising:
polymerizing a first hydrogel precursor solution containing a chemical initiator and optionally fluorescent particles onto surface of a first substrate and second substrate that have been chemically activated with glutaraldehyde or methacrylate in order to form a first hydrogel on the first substrate and second hydrogel on the second substrate;
forming a polydimethylsiloxane (PDMS) mold comprising the hydrogel of the first substrate;
puncturing the PDMS mold to provide inlet and outlet flow paths;
treating the second substrate comprising the second hydrogel and the PDMS mold comprising the first hydrogel with UV-Ozone;
bonding the PDMS mold to the second substrate at an elevated temperature to form a fluidics chamber, wherein the bond is chemically and irreversibly formed.

21. The method of claim 20, further comprising equilibrating the first and second hydrogel to physiological pH and osmolarity by using a buffered solution.

22. The method of claim 1, wherein the cell composition comprises a hydrogel precursor solution containing a photoinitiator and suspended cells.

23. The method of claim 1, wherein part (d) comprise identifying cellular islands;
forming a patterned hydrogel comprising the cellular islands by using a photomask which is placed under the fluidics chamber of the device, and a UV light of a wavelength of about 365±40 nm is shone onto the cellular island; and
removing excess unreacted hydrogel precursor solution from the fluidics chamber by washing with a buffered solution.

24. A method for determining the effects of a pharmaceutically active agent on cells comprising:
introducing the pharmaceutically active agent in a carrier into the microfluidic device of claim 1, and comparing the effects of the agent on the cells in comparison to the carrier alone.

* * * * *